(12) United States Patent
Kang

(10) Patent No.: US 12,268,458 B2
(45) Date of Patent: Apr. 8, 2025

(54) INTEGRATED ROBOTIC SURGERY SYSTEM

(71) Applicant: MAKO Surgical Corp., Weston, FL (US)

(72) Inventor: Hyosig Kang, Weston, FL (US)

(73) Assignee: MAKO Surgical Corp., Weston, FL (US)

( * ) Notice: Subject to any disclaimer, the term of this patent is extended or adjusted under 35 U.S.C. 154(b) by 470 days.

(21) Appl. No.: 17/866,890

(22) Filed: Jul. 18, 2022

(65) Prior Publication Data

US 2022/0354601 A1 Nov. 10, 2022

Related U.S. Application Data

(63) Continuation of application No. 17/330,055, filed on May 25, 2021, now Pat. No. 11,419,688, which is a
(Continued)

(51) Int. Cl.
*A61B 34/30* (2016.01)
*A61B 6/00* (2024.01)
(Continued)

(52) U.S. Cl.
CPC ............ *A61B 34/30* (2016.02); *A61B 6/4441* (2013.01); *A61B 6/4429* (2013.01); *A61B 6/4452* (2013.01);
(Continued)

(58) Field of Classification Search
CPC ... A61B 6/4429; A61B 6/4441; A61B 6/4452; A61B 6/4458; A61B 6/4476; A61B 6/46;
(Continued)

(56) References Cited

U.S. PATENT DOCUMENTS

| | | | |
|---|---|---|---|
| 4,280,580 A | 7/1981 | Wojcik | |
| 5,835,558 A | 11/1998 | Maschke | |

(Continued)

FOREIGN PATENT DOCUMENTS

| | | |
|---|---|---|
| DE | 10352197 A1 | 8/2005 |
| DE | 10 2008 022 924 A1 | 11/2009 |
| WO | WO-02/065931 A1 | 8/2002 |

OTHER PUBLICATIONS

International Search Report and Written Opinion for PCT Application No. PCT/US2013/078533, mail date Apr. 28, 2014, 12 pages.

*Primary Examiner* — Robert A Lynch
(74) *Attorney, Agent, or Firm* — FOLEY & LARDNER LLP

(57) ABSTRACT

A surgery system includes a mechanical hub, an anatomy support structure coupled to the mechanical hub, a first moveable support structure, and an imaging system comprising a source element and a detector element. The imaging system is coupled to the mechanical hub via the first moveable support structure such that the source element and the detector element are repositionable relative to the anatomy support structure. The surgical system also includes a second moveable support structure coupled to the mechanical hub and a surgical instrument coupled to the mechanical hub via the second moveable support structure.

20 Claims, 43 Drawing Sheets

Related U.S. Application Data continuation of application No. 16/025,374, filed on Jul. 2, 2018, now Pat. No. 11,083,530, which is a continuation of application No. 14/145,719, filed on Dec. 31, 2013, now Pat. No. 10,028,788.

(60) Provisional application No. 61/747,854, filed on Dec. 31, 2012.

(51) Int. Cl.
*A61B 34/20* (2016.01)
*A61B 90/00* (2016.01)
*A61B 90/50* (2016.01)

(52) U.S. Cl.
CPC .......... *A61B 6/4458* (2013.01); *A61B 6/4476* (2013.01); *A61B 34/20* (2016.02); *A61B 2090/376* (2016.02); *A61B 90/50* (2016.02)

(58) Field of Classification Search
CPC ......... A61B 6/461; A61B 6/462; A61B 6/463; A61B 6/464; A61B 6/465; A61B 34/00; A61B 34/20; A61B 34/30; A61B 2034/2055; A61B 90/50; A61B 2090/376; A61B 2090/3764; A61B 2090/508
See application file for complete search history.

(56) References Cited

U.S. PATENT DOCUMENTS

| | | |
|---|---|---|
| 6,139,183 A | 10/2000 | Graumann |
| 6,213,638 B1 | 4/2001 | Rattner |
| 6,234,672 B1 | 5/2001 | Tomasetti et al. |
| 6,246,200 B1 | 6/2001 | Blumenkranz et al. |
| 2003/0153978 A1 | 8/2003 | Whiteside |
| 2004/0076259 A1 | 4/2004 | Jensen et al. |
| 2005/0053192 A1 | 3/2005 | Sukovic et al. |
| 2005/0075561 A1 | 4/2005 | Golden |
| 2005/0075563 A1* | 4/2005 | Sukovic ............... A61B 6/469 600/427 |
| 2006/0142657 A1* | 6/2006 | Quaid ................. A61B 90/37 600/424 |
| 2006/0241405 A1 | 10/2006 | Leitner et al. |
| 2007/0142970 A1 | 6/2007 | Burbank et al. |
| 2007/0211863 A1 | 9/2007 | Graumann et al. |
| 2008/0004523 A1 | 1/2008 | Jensen |
| 2009/0088634 A1 | 4/2009 | Zhao et al. |
| 2009/0234444 A1 | 9/2009 | Maschke |
| 2010/0166496 A1 | 7/2010 | Bennett et al. |
| 2010/0234770 A1 | 9/2010 | Colombet et al. |
| 2011/0276179 A1 | 11/2011 | Banks et al. |
| 2014/0183607 A1 | 7/2014 | Liu |

* cited by examiner

INTEGRATED ROBOTIC SURGERY SYSTEM

CROSS-REFERENCE TO RELATED APPLICATION

This application is a continuation of U.S. patent application Ser. No. 17/330,055, filed May 25, 2021, which is a continuation of U.S. patent application Ser. No. 16/025,374, filed Jul. 2, 2018, which is a continuation of U.S. patent application Ser. No. 14/145,719 filed Dec. 31, 2013, which claims the benefit of and priority to U.S. Provisional Patent Application No. 61/747,854, filed Dec. 31, 2012, each of which is incorporated by reference herein in its entirety.

BACKGROUND

The present invention relates generally to robotic surgery techniques, and more particularly to configurations which may be utilized to efficiently facilitate intraoperative imaging by fluoroscopy during surgical procedures such as joint resurfacing or replacement.

With continued surgery-related diagnostic and treatment specialization, and increases in the costs associated with maintaining and staffing operating room space, there is a continued need for capital equipment technologies and configurations that facilitate flexibility and efficiency. For example, radiography and fluoroscopy systems for providing intraoperative images during procedures such as orthopedic surgery conventionally have included relatively large and unwieldly hardware configurations, such as the conventional fluoroscopy C-arm system 2 depicted in FIG. 1A, generally including a source 6 and a detector 8 fixedly coupled by a C-arm connecting structure 4, and the conventional flat-panel radiography system 10 depicted in FIG. 1B which is partially ceiling-mounted and partially floor mounted. Operation of these systems generally requires moving one or more moveable portions into a position and/or orientation relative to one or more subject tissue structures of a patient, and often repositioning and/or reorienting to capture additional images from another viewpoint relative to the tissue structures. For example, in the case of many joint arthroplasty related procedures, it will be of interest for the surgeon to gather both antero/posterior and lateral views of the particular skeletal joint of interest, and gathering both views will require movements, either manually or electromechanically induced, of the various portions of imaging hardware. Further, it is sometimes the case that the anatomy of interest of the patient will move during the procedure, potentially requiring re-alignment of the imaging hardware to procure additional intraoperative views. In addition, with the onset of robotic interventional systems and tools, such as system 12 depicted in FIG. 2 and sold under the tradename RIO® by MAKO Surgical Corporation of Fort Lauderdale, Florida (including a mobile base 14 and an instrument 18, such as a bone cutting instrument, coupled to the mobile base 14 by an articulated robotic arm 16), workflow can be interrupted by trading an interventional system and an imaging system in and out of the space most adjacent the patient tissue structures of interest during the procedure, which may require re-registration of the interventional and/or imaging systems each time relative to the patient anatomy.

SUMMARY

One embodiment is directed to a robotic surgery system having a mobile base configured to be moveable into and out of an operating room when in a freewheeling mode, and fixed relative to the operating room when in a braked mode. The system further includes a first moveable support structure coupled between the mobile base and a first element of a fluoroscopic imaging system. The first element includes one of a source element and a detector element and a second element of the fluoroscopic imaging system includes the other of the source element and the detector element. The second element is configured to be repositionable relative to a patient tissue structure disposed between the first and second elements of the fluoroscopic imaging system. The system further includes a coupling member configured to fixedly couple the first element of the fluoroscopic imaging system to the second element and a surgical instrument configured for conducting a procedure on the patient tissue structure. The system further includes a second moveable support structure coupled between the coupling member and the surgical instrument, wherein the second moveable support structure includes one or more actuators which may be controlled to electromechanically characterize movement of the surgical instrument relative to the coupling member.

The first moveable support structure may include an electromechanically-controllable robotic arm. The robotic arm may include one or more joints and one or more motors configured to controllably regulate motion at the one or more joints. The system further may include at least one sensor configured to monitor a position of at least a portion of the electromechanically-controllable robotic arm. The at least one sensor may be selected from the group consisting of: an encoder, a potentiometer, an optical position tracker, and an electromagnetic position tracker. The system further may include a controller coupled to the electromechanically-controllable robotic arm and at least one sensor, the controller configured to cause the electromechanically-controllable robotic arm to move at least in part in response to one or more signals received from the at least one sensor. The first element may be the source element and the second element may be the detector element. The first element may be the detector element and the second element may be the source element. The source element may be configured to produce a collimated beam having a cross-sectional shape selected from the group consisting of: a circle, an ellipse, a square, and a rectangle. The detector element may be a flat panel detector. The flat panel detector may be an amorphous silicon panel detector. The flat panel detector may be a CMOS fluoroscopy panel. The flat panel detector may have an effective image area having a shape selected from the group consisting of: a circle, an ellipse, a square, and a rectangle. The flat panel detector may have a rectangular CMOS active fluoroscopy panel having dimensions of about 5 inches by about 6 inches. The surgical instrument may include a bone cutting tool. The bone cutting tool may include a motor. The bone cutting cool may include a bone cutting element selected from the group consisting of: a rotary cutting burr, an insertion/retraction motion reciprocal cutting saw, and a lateral reciprocal motion cutting saw. The coupling member may include a substantially rigid member shaped to form a recess between the first and second elements of the fluoroscopic imaging system, the recess configured to accommodate placement of the patient tissue structure between the first and second elements. The coupling member may be a C-arm. The system further may include a coupler configured to at least transiently couple a portion of the coupling member to a portion of an operating table configured to support the patient tissue structure. The coupler may be manually-activated. The coupler may be electromechanically-activated. The second moveable support structure may include an electromechanically-controllable robotic arm. The robotic arm may include one or more joints and one or more motors configured to controllably regulate motion at the one or mere joints. The system further may include at least one sensor configured to monitor a position of at least a portion of the electromechanically-controllable robotic arm. The at least one sensor may be at least one of an encoder, a potentiometer, an optical position tracker, and an electromagnetic position tracker. The system further may include a controller coupled to the electromechanically-controllable robotic arm and at least one sensor, the controller configured to resist movement of the electromechanically-controllable robotic arm based at least in part upon one or more signals received from the at least one sensor. The system further may include a controller operatively coupled to the one or more actuators of the second moveable support structure and configured to receive signals from a sensing system operatively coupled to the controller, the sensing system configured to detect positions of one or more sensor elements coupled to the patient tissue structure. The controller may be operatively coupled to the surgical instrument and configured to modify one or more degrees of freedom of movement of the surgical instrument relative to the patient tissue structure in response to the signals from the sensing system. The controller may be configured to actively inhibit movement of the surgical instrument in one or more directions in response to the signals from the sensing system. The sensing system may be one of an optical sensing system, an electromagnetic sensing system, and a joint rotation sensing system. The one or more sensor elements may be one of a reflective marker, an electromagnetic localization sensor, a strain gauge, rotation encoder, and a joint rotation potentiometer. The system further may include sensor elements coupled to the first moveable support structure, wherein the controller is configured to detect motion of the first moveable support structure. The system further may include sensor elements coupled to the second moveable support structure, wherein the controller is configured to detect motion of the first moveable support structure. The system further may include a user interface configured to allow for an operator to select a desired geometric relationship between the first and second elements relative to the patient tissue structure.

The invention is capable of other embodiments and of being practiced or being carried out in various ways. Alternative exemplary embodiments relate to other features and combinations of features as may be generally recited in the claims.

BRIEF DESCRIPTION OF THE FIGURES

The invention will become more fully understood from the following detailed description, taken in conjunction with the accompanying drawings, wherein like reference numerals refer to like elements, in which.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

Figure 1A:
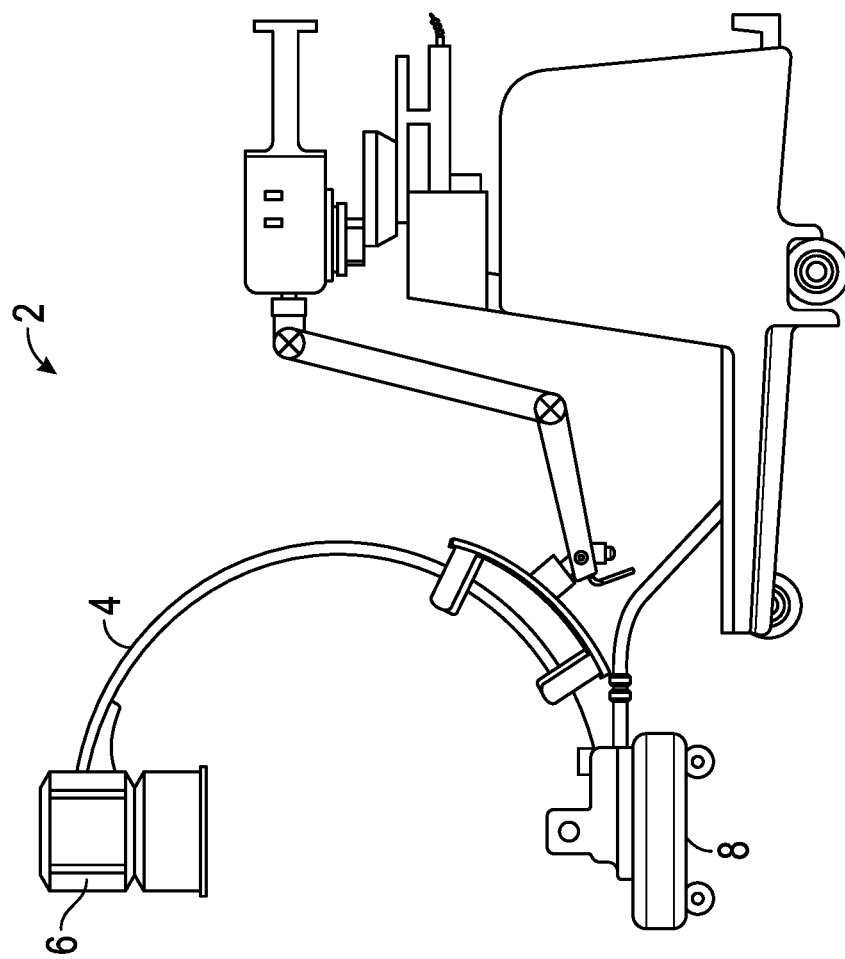
FIG. 1A depicts a conventional fluoroscopic imaging system with a C-arm coupling a source and a detector.
Figure 1A:
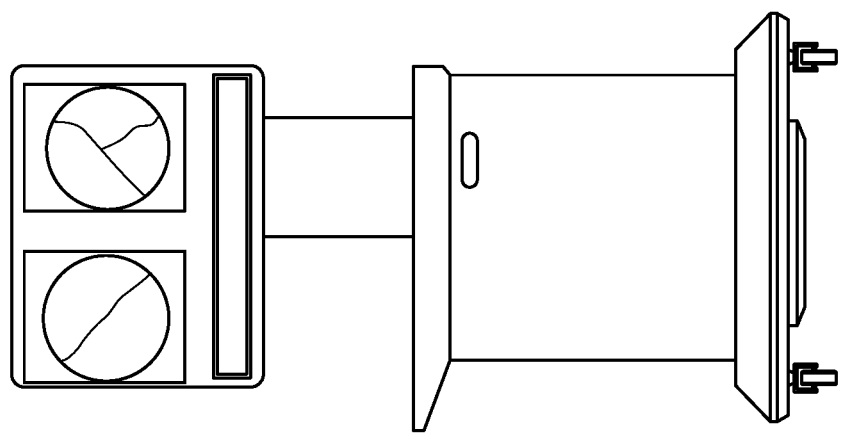
Figure 1B:
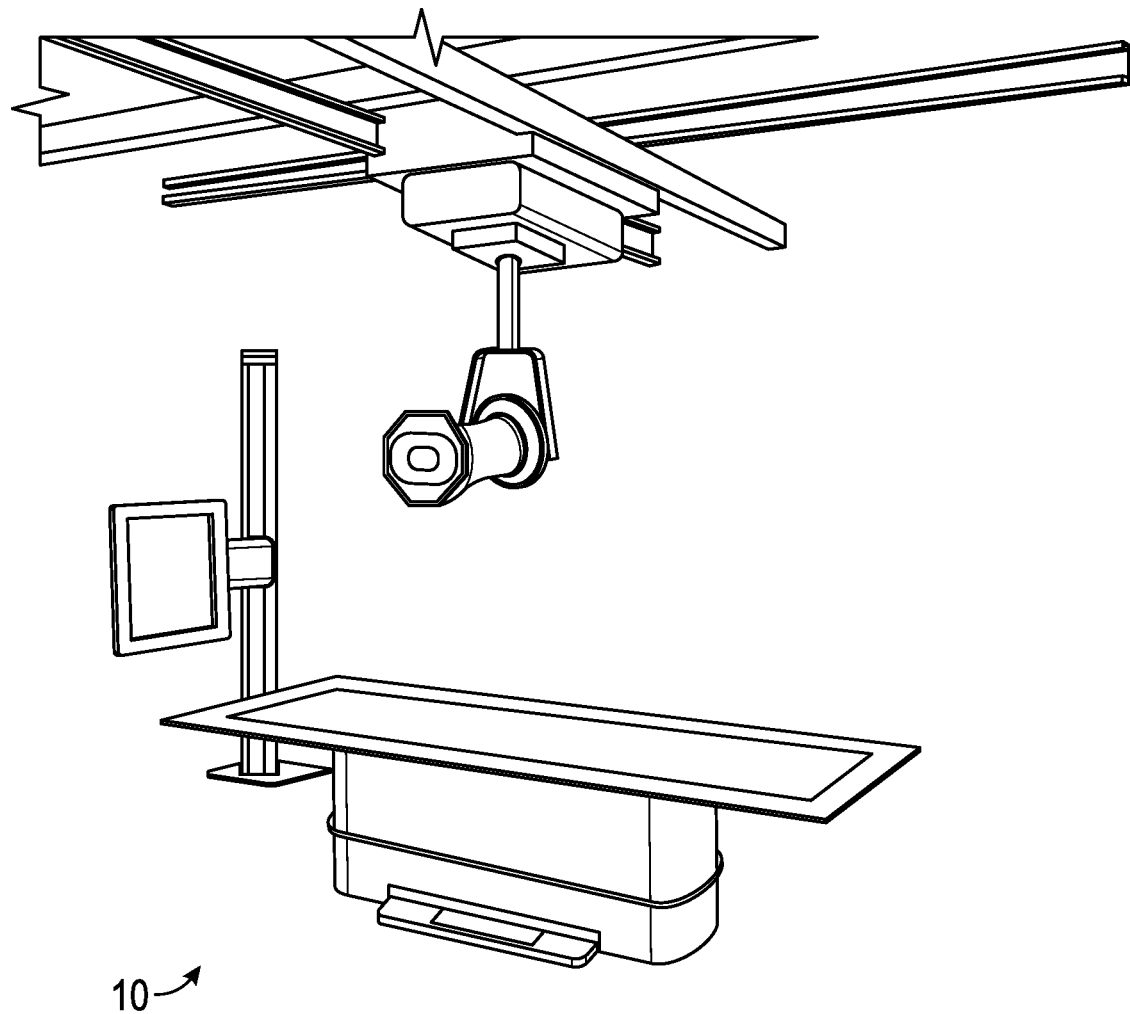
FIG. 1B depicts a conventional radiographic imaging system with a flat panel detector.
Figure 2:
FIG. 2 depicts a robotic surgery system with a mobile base.
Figure 3A:
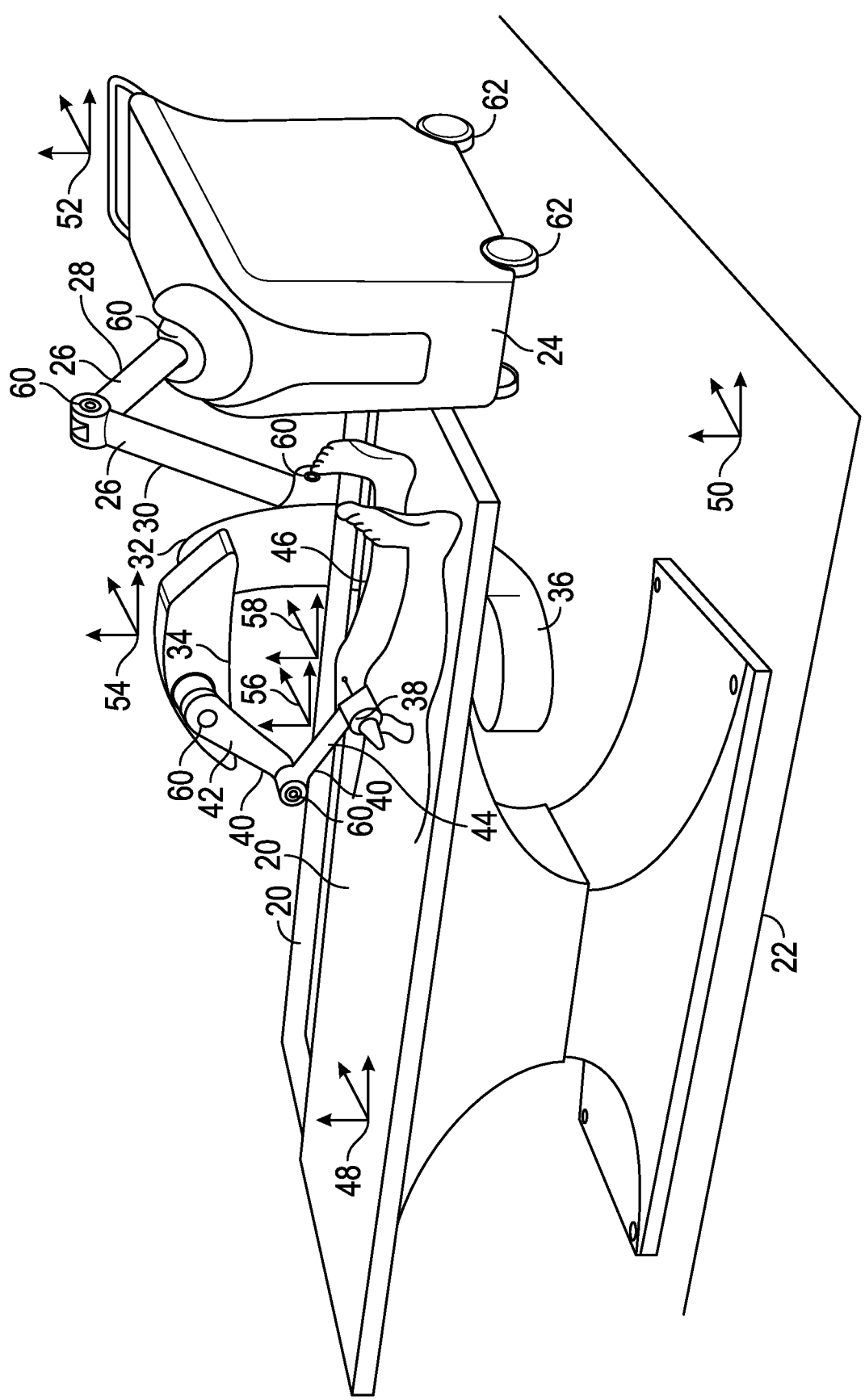
FIG. 3A depicts one embodiment of a robotic surgery system with integrated imaging capabilities.
Figure 3B:
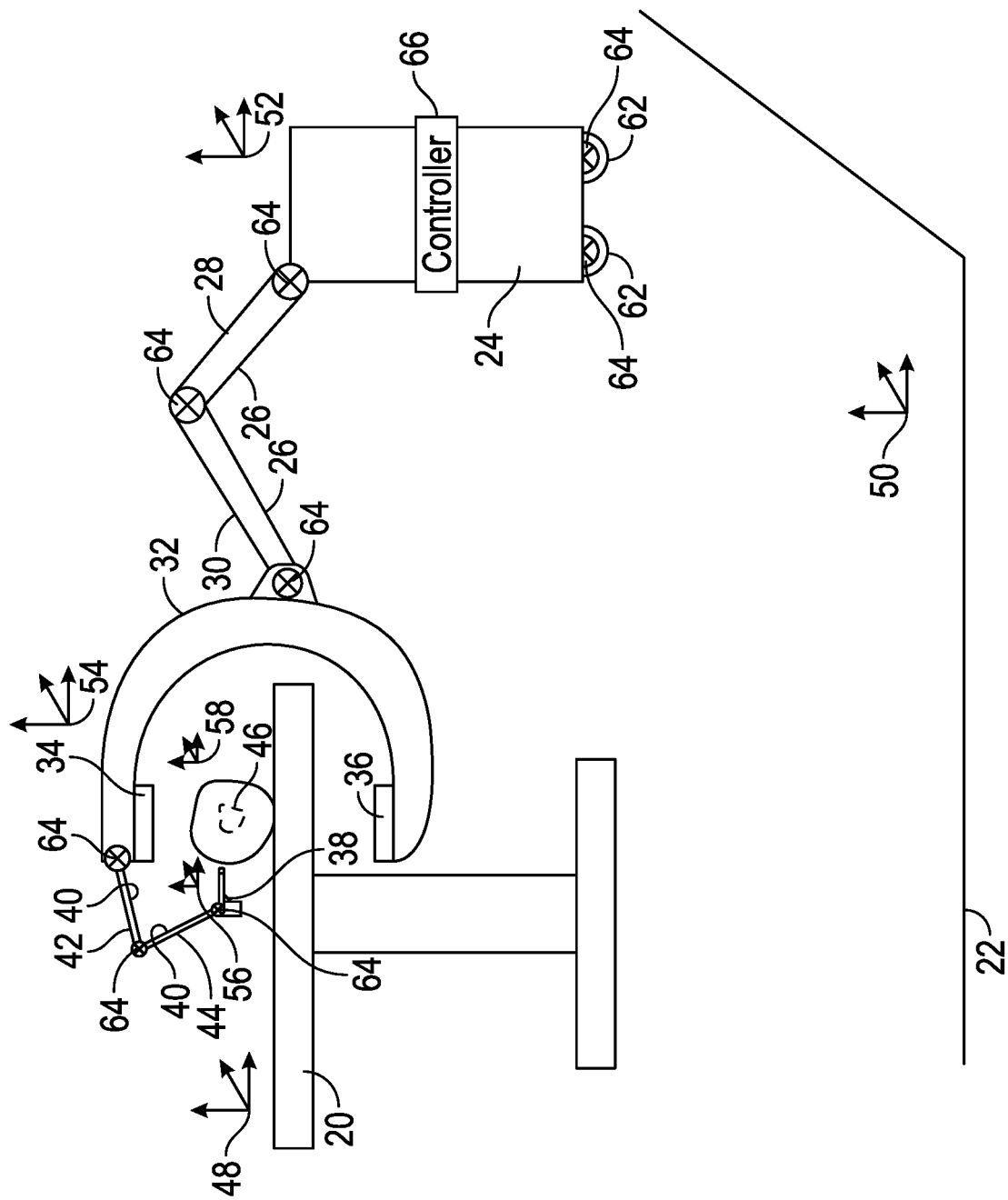
FIG. 3B depicts one embodiment of a robotic surgery system with integrated imaging capabilities.
Figure 3C:
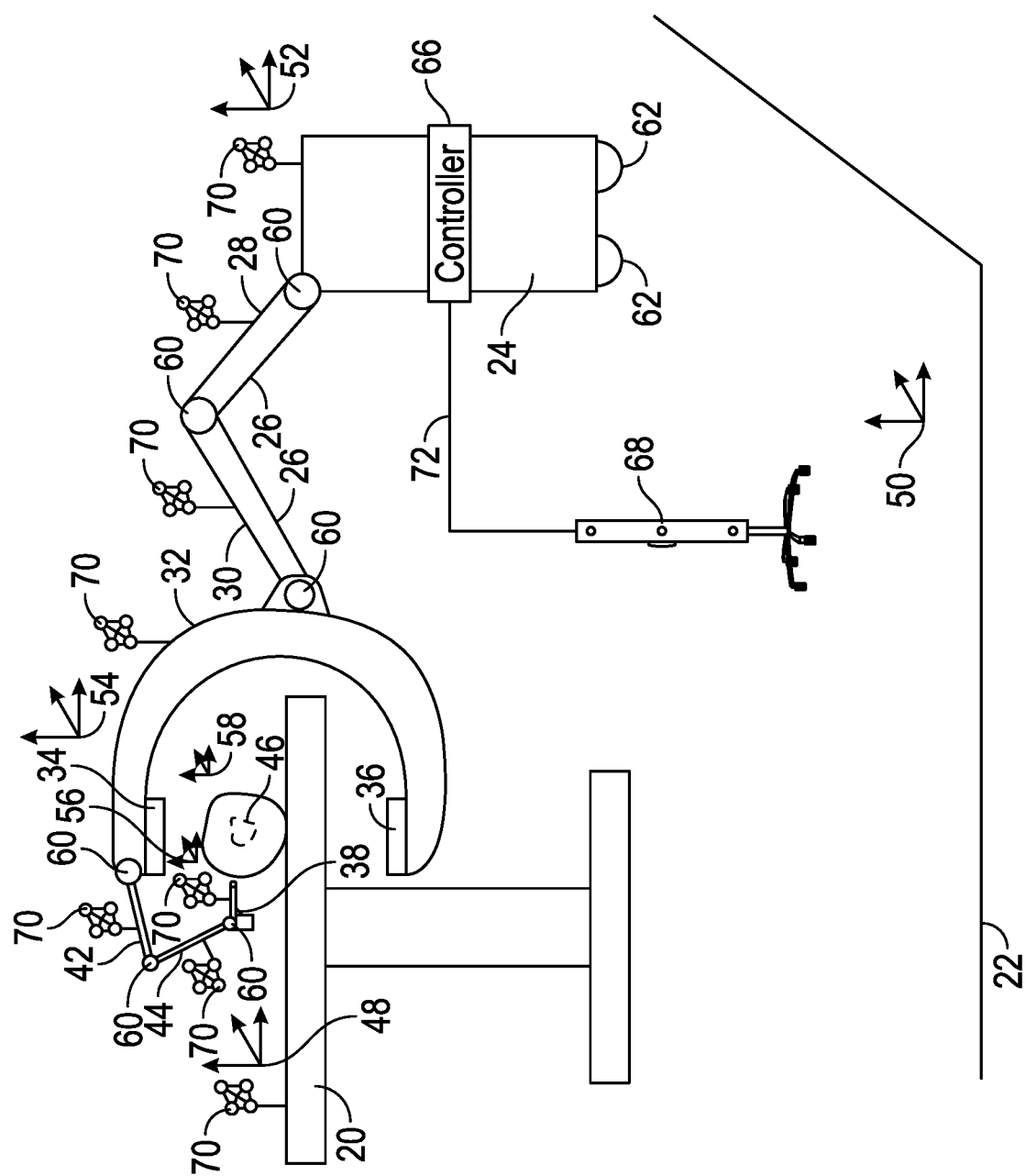
FIG. 3C depicts one embodiment of a robotic surgery system with integrated imaging capabilities.
Figure 3D:
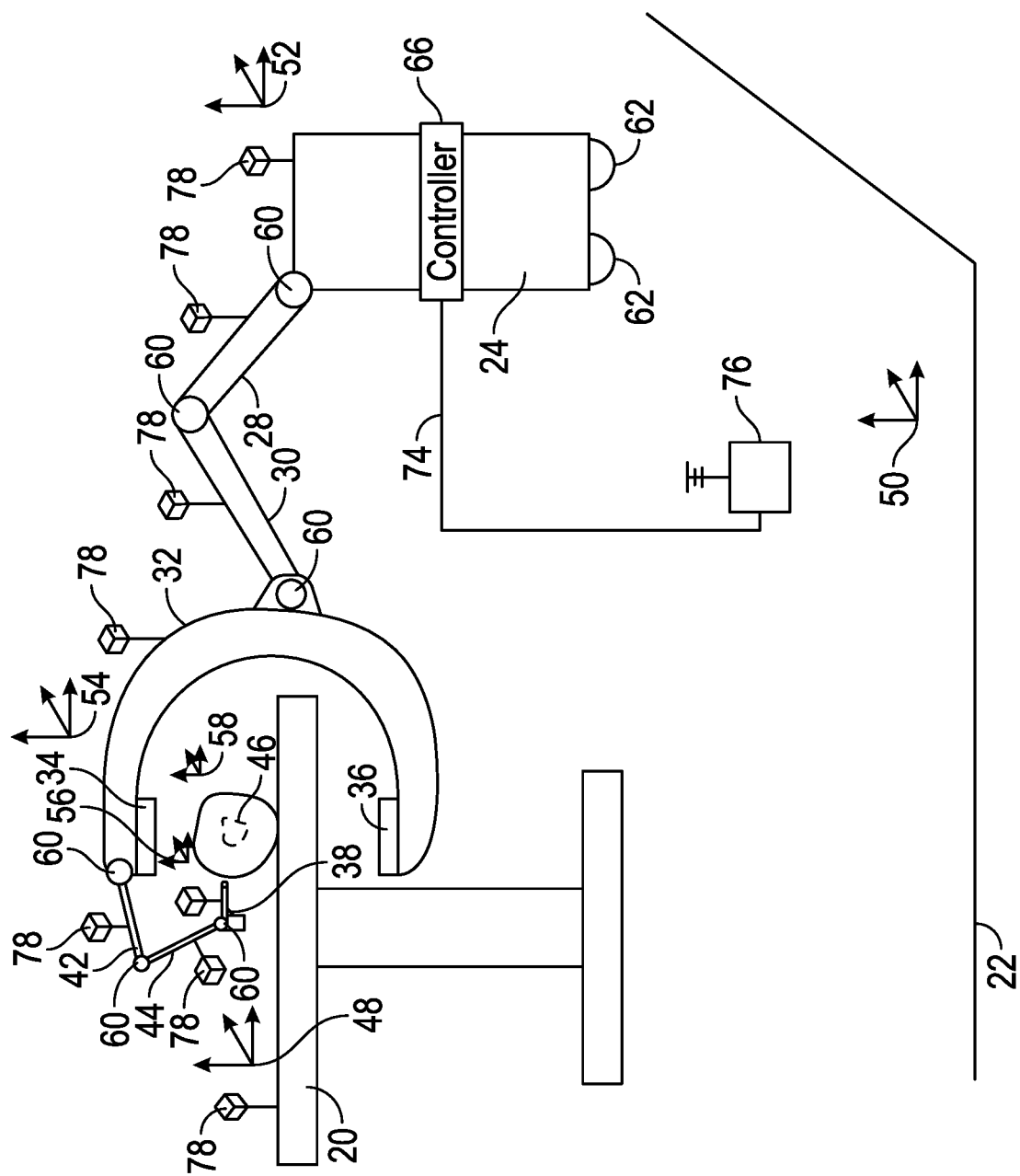
FIG. 3D depicts one embodiment of a robotic surgery system with integrated imaging capabilities.
Figure 3E:
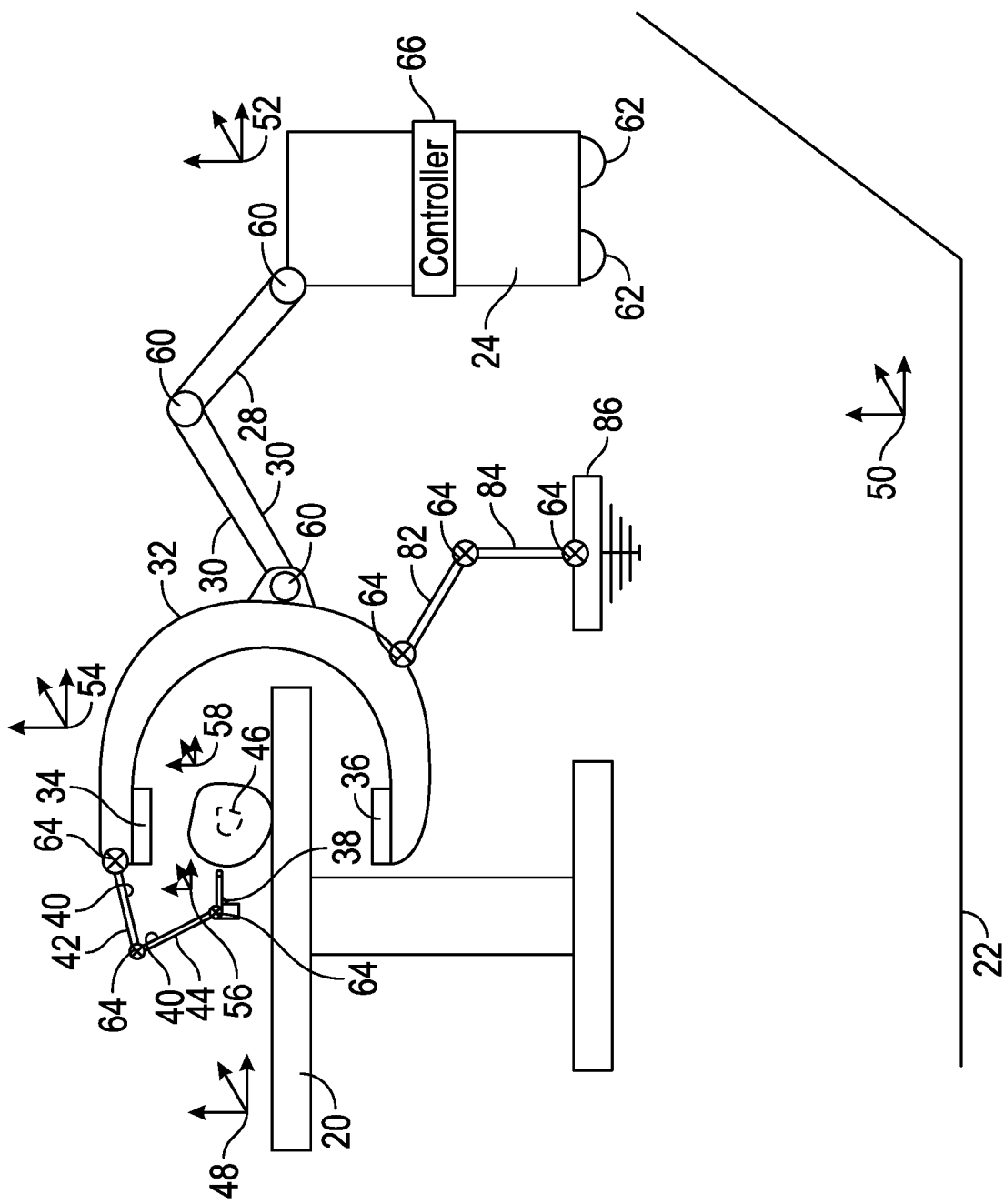
FIG. 3E depicts one embodiment of a robotic surgery system with integrated imaging capabilities.
Figure 3F:
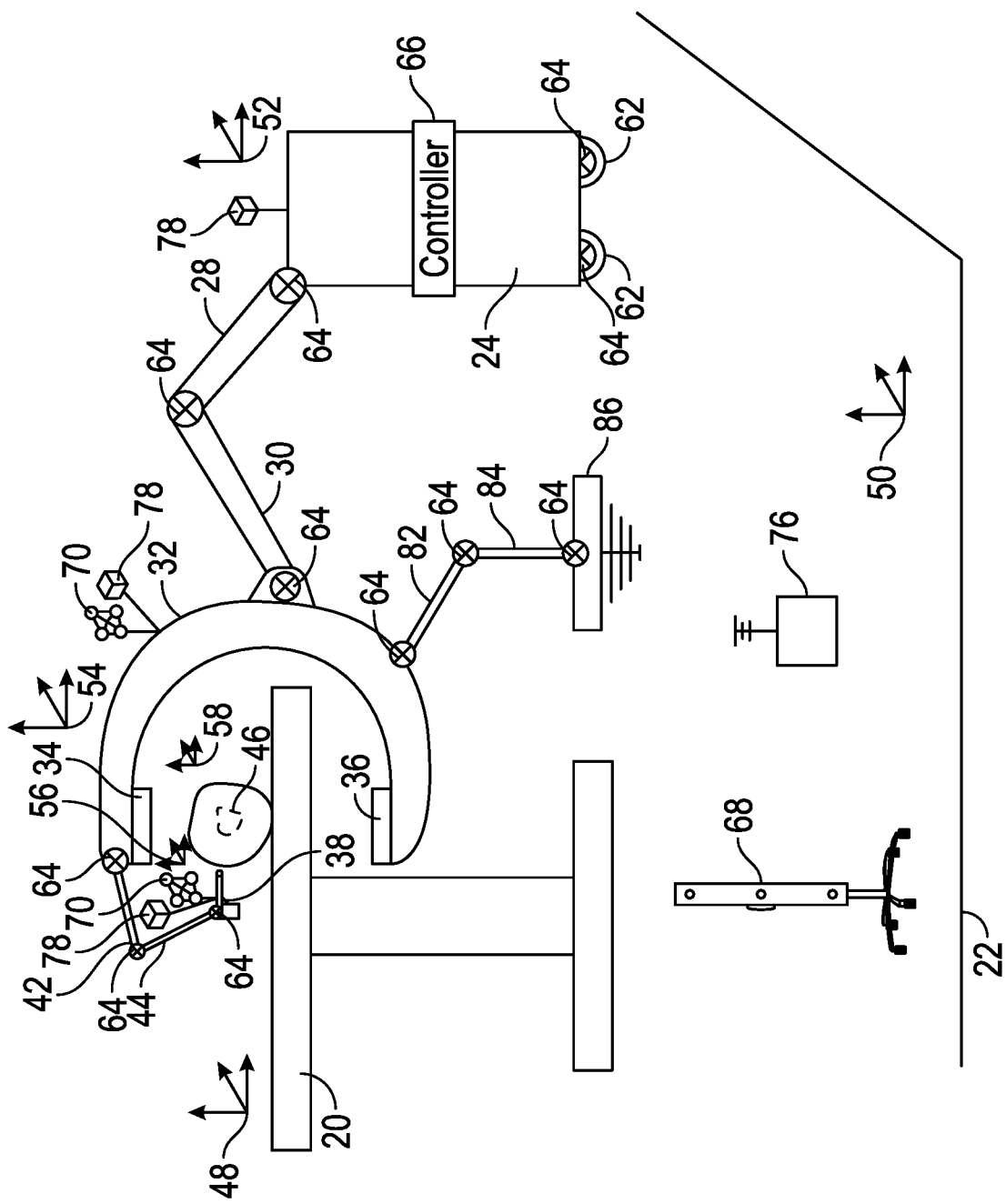
FIG. 3F depicts one embodiment of a robotic surgery system with integrated imaging capabilities.
Figure 3G:
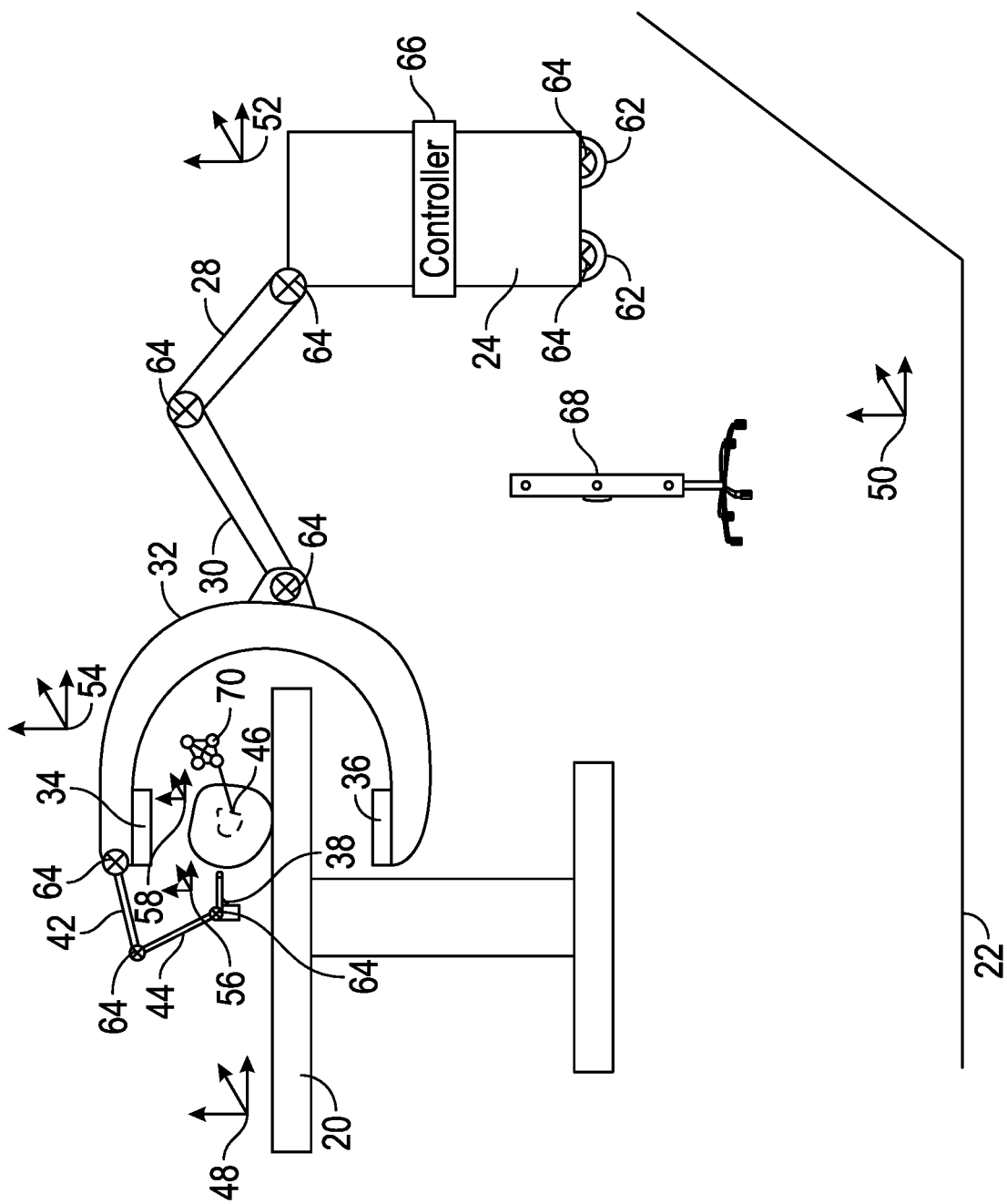
FIG. 3G depicts one embodiment of a robotic surgery system with integrated imaging capabilities.
Figure 3H:
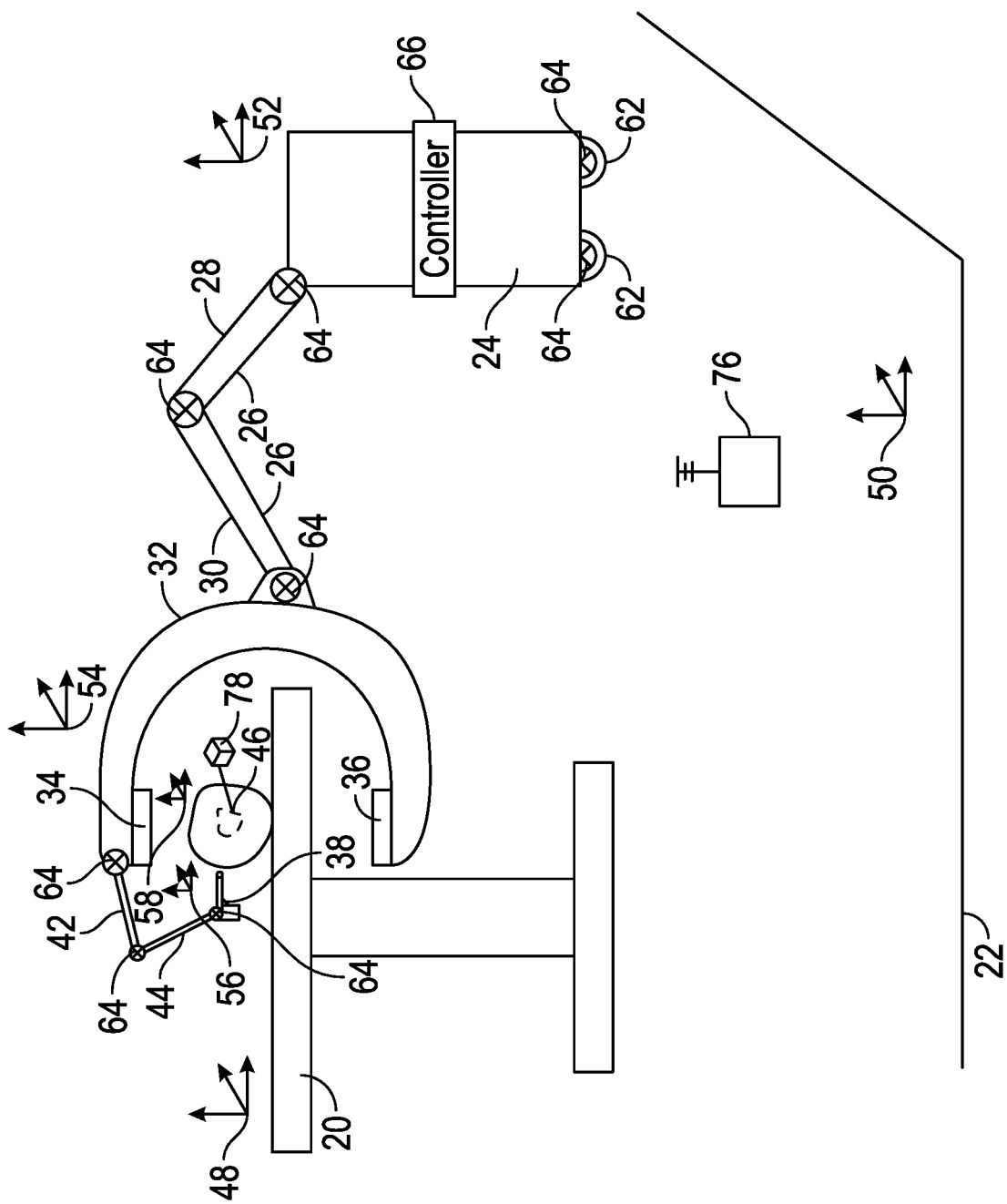
FIG. 3H depicts one embodiment of a robotic surgery system with integrated imaging capabilities.
Figure 3I:
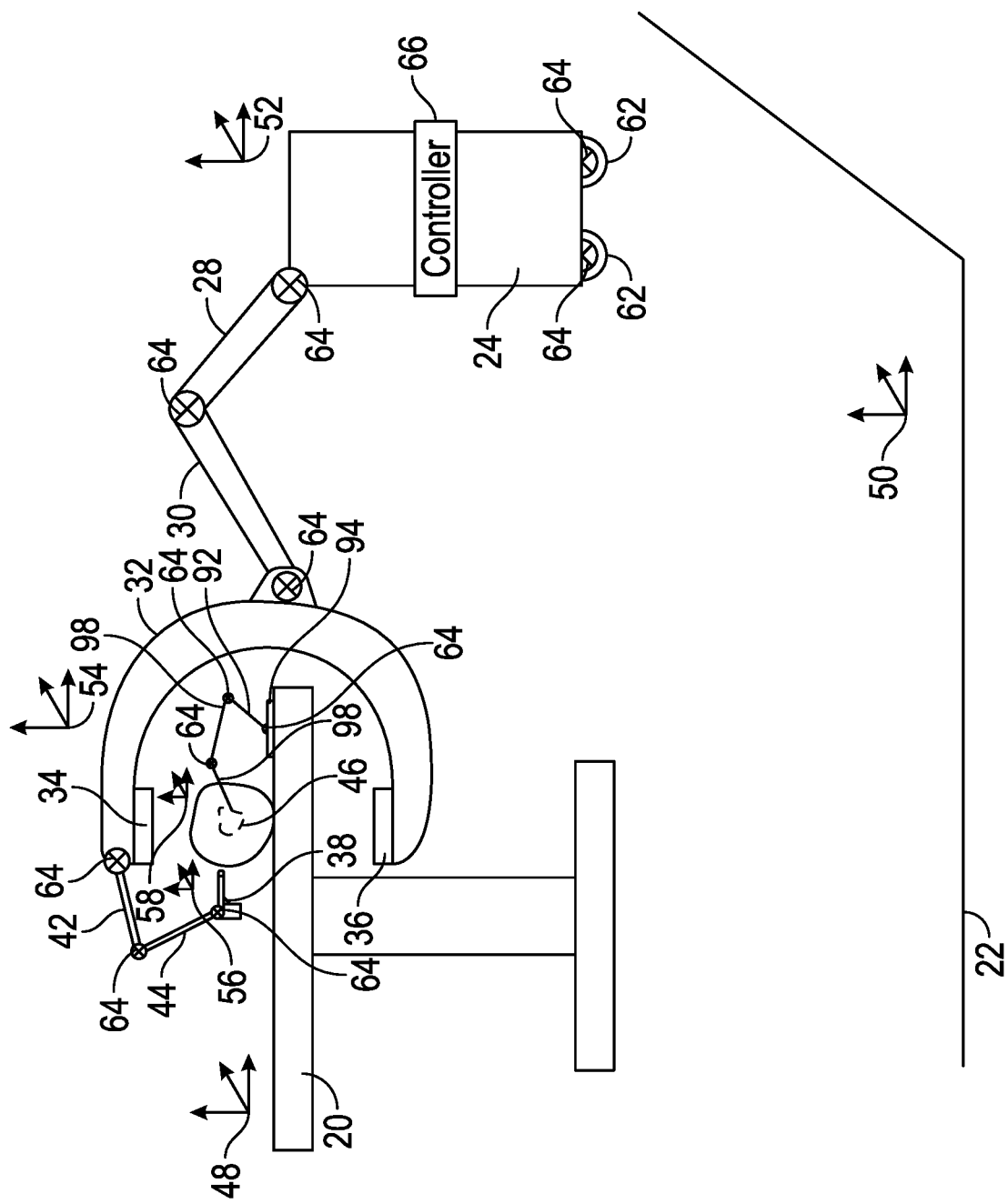
FIG. 3I depicts one embodiment of a robotic surgery system with integrated imaging capabilities.
Figure 3J:
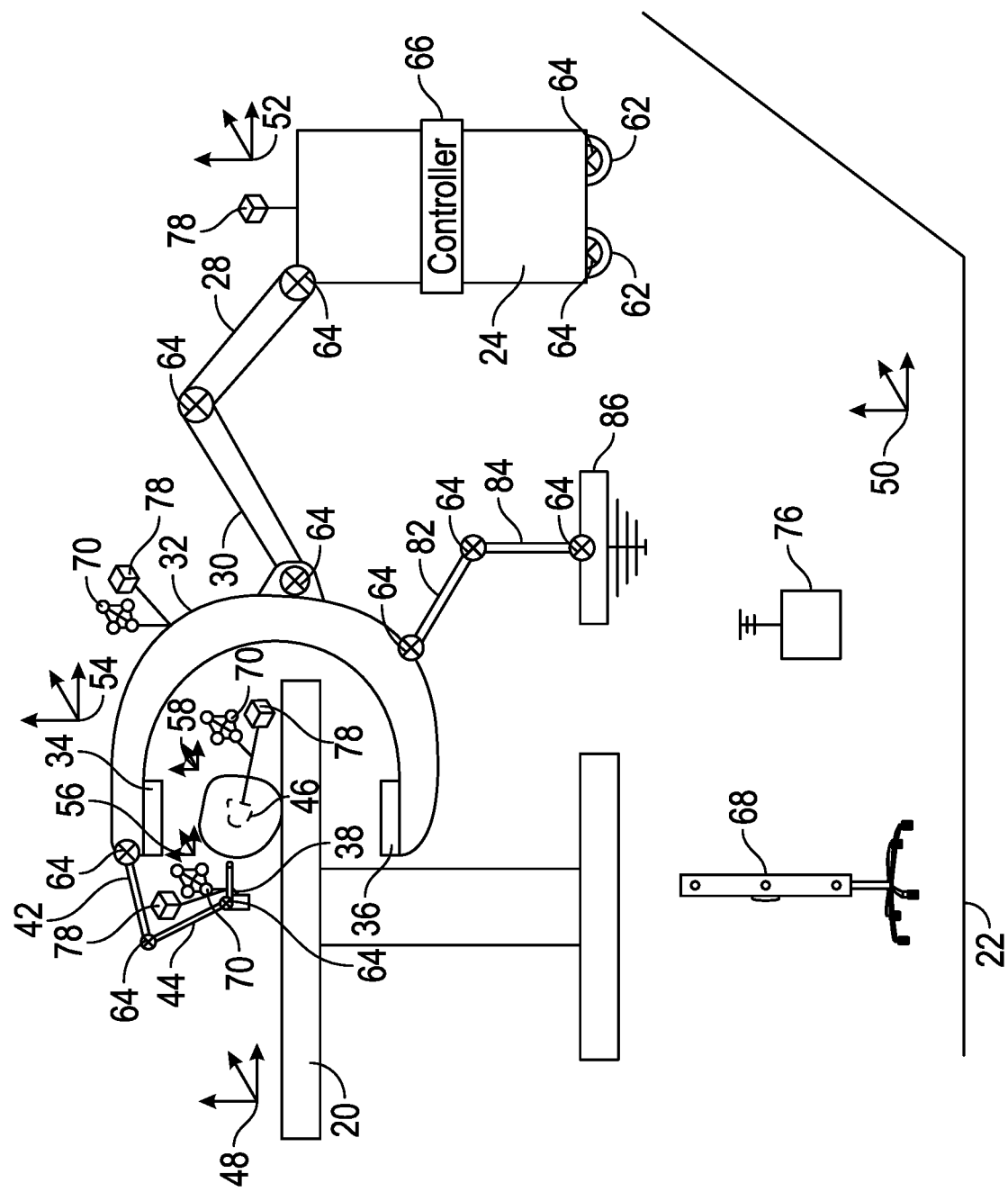
FIG. 3J depicts one embodiment of a robotic surgery system with integrated imaging capabilities.
Figure 3K:
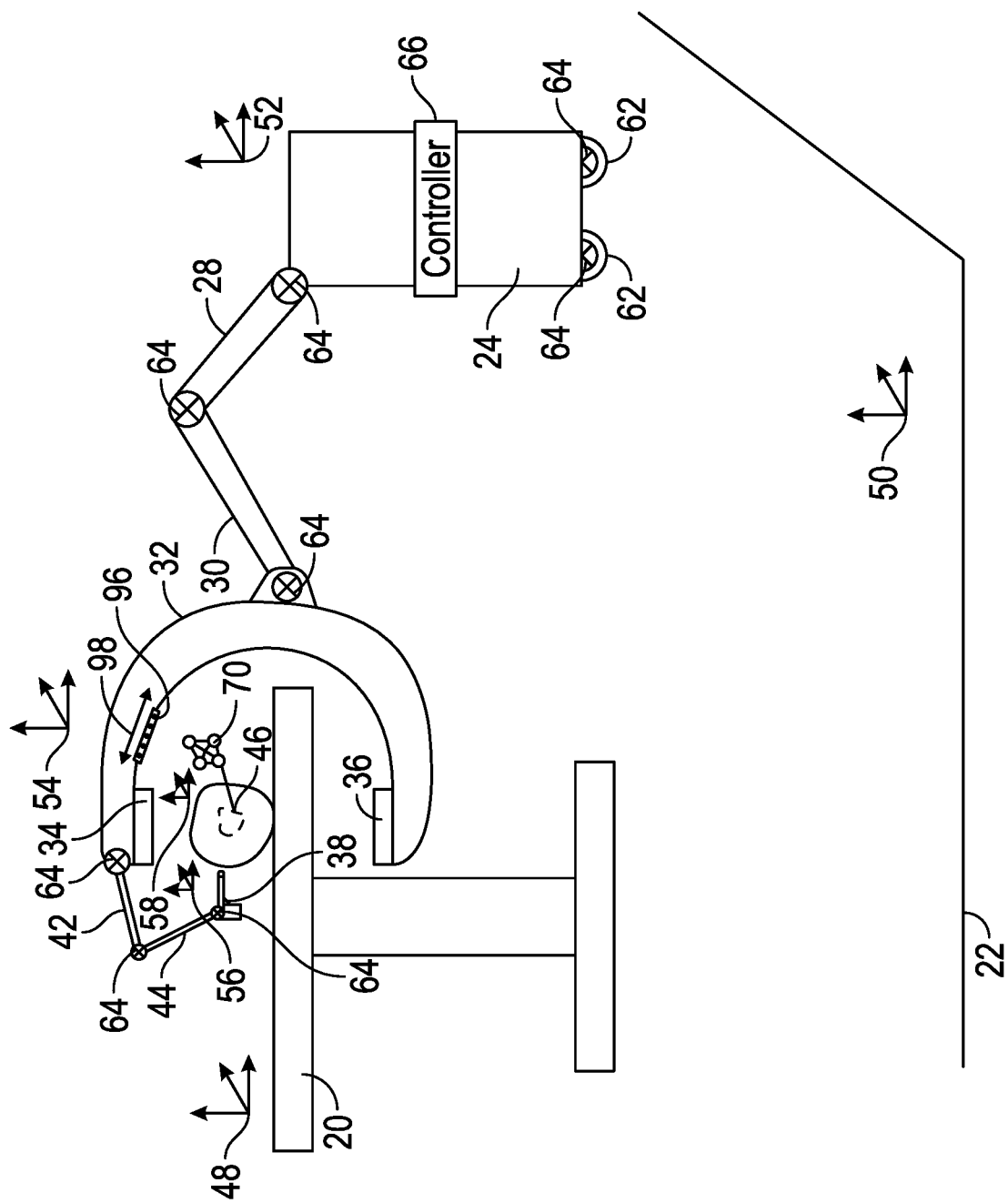
FIG. 3K depicts one embodiment of a robotic surgery system with integrated imaging capabilities.
Figure 3L:
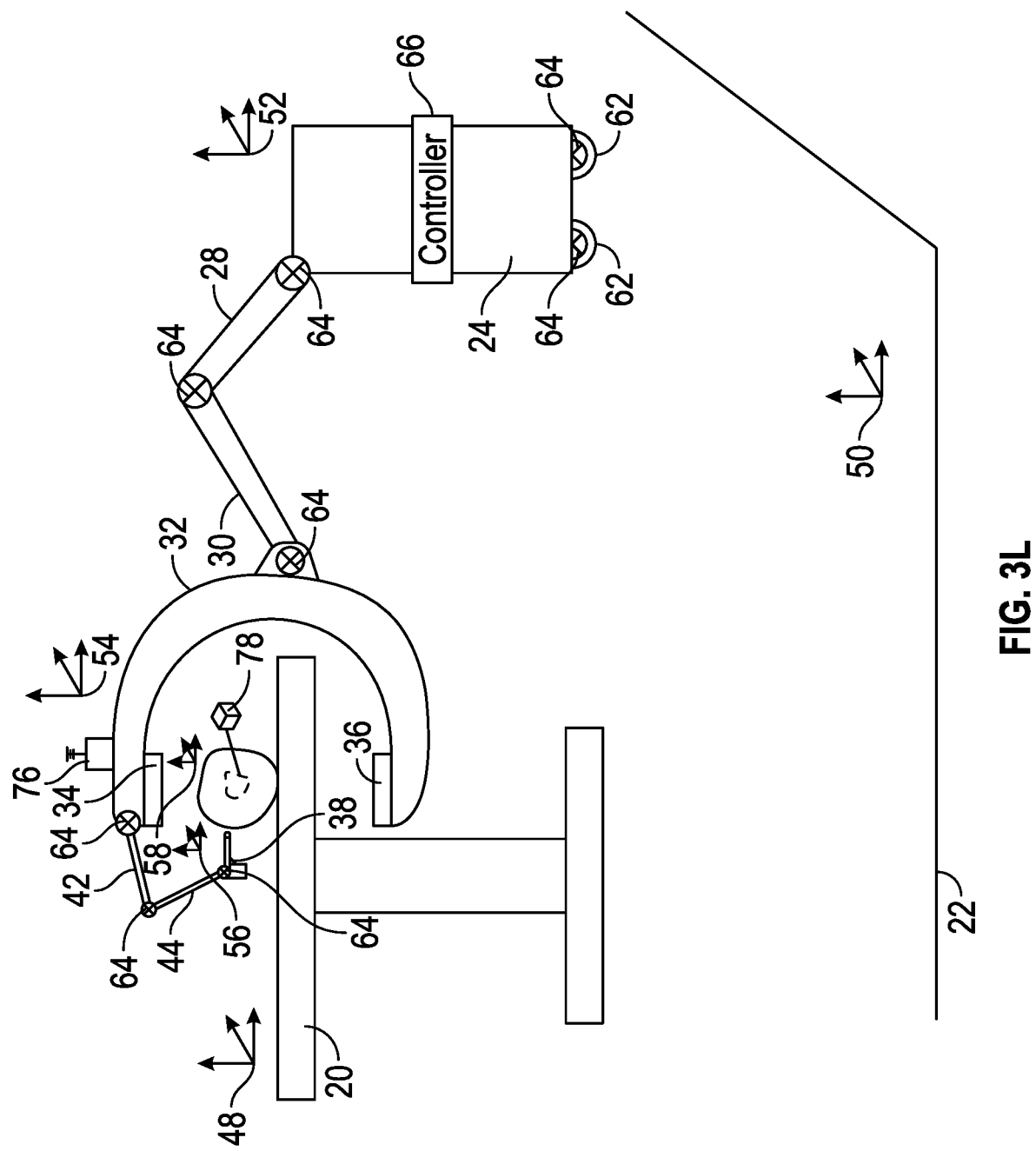
FIG. 3L depicts one embodiment of a robotic surgery system with integrated imaging capabilities.
Figure 3M:
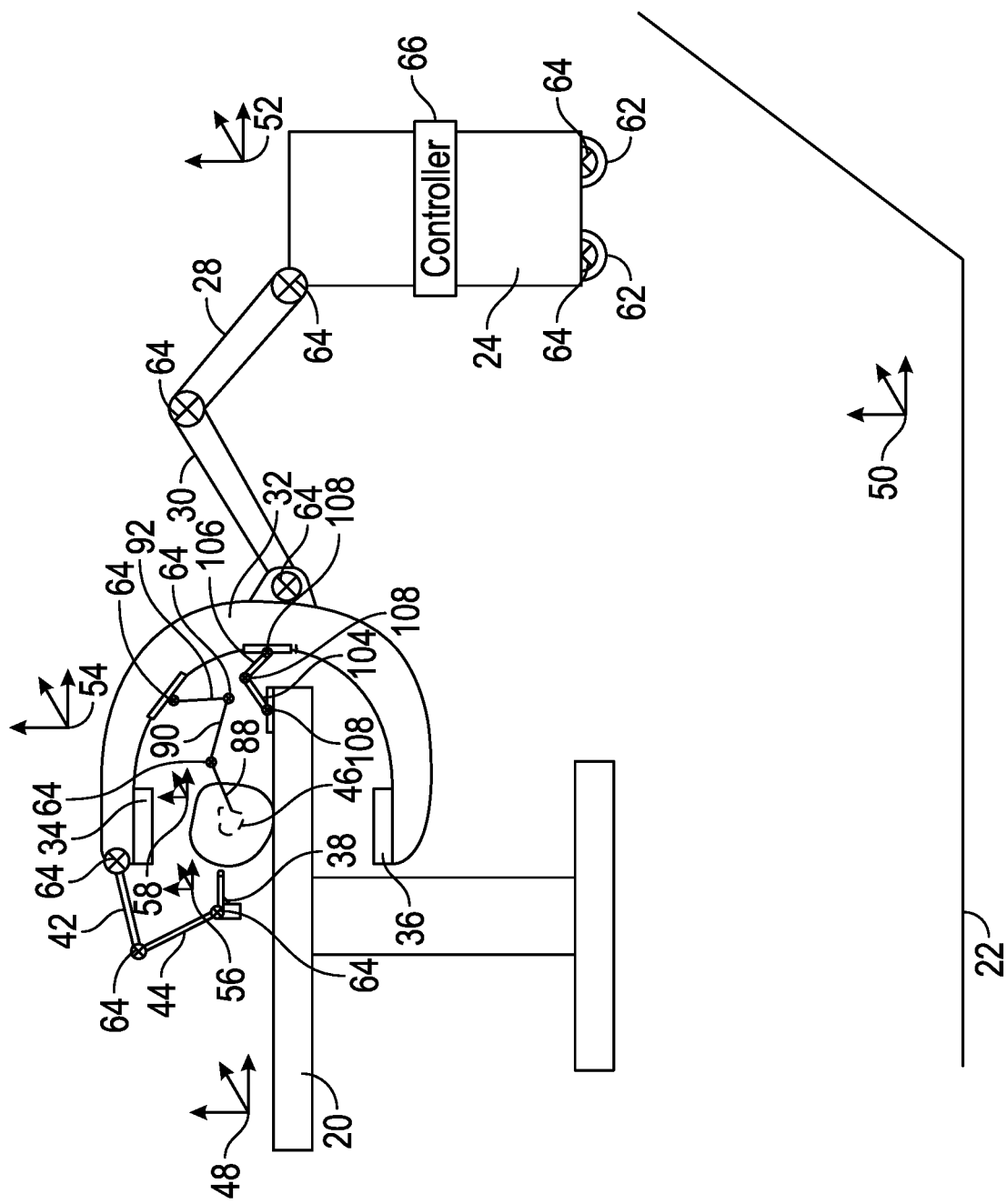
FIG. 3M depicts one embodiment of a robotic surgery system with integrated imaging capabilities.
Figure 3N:
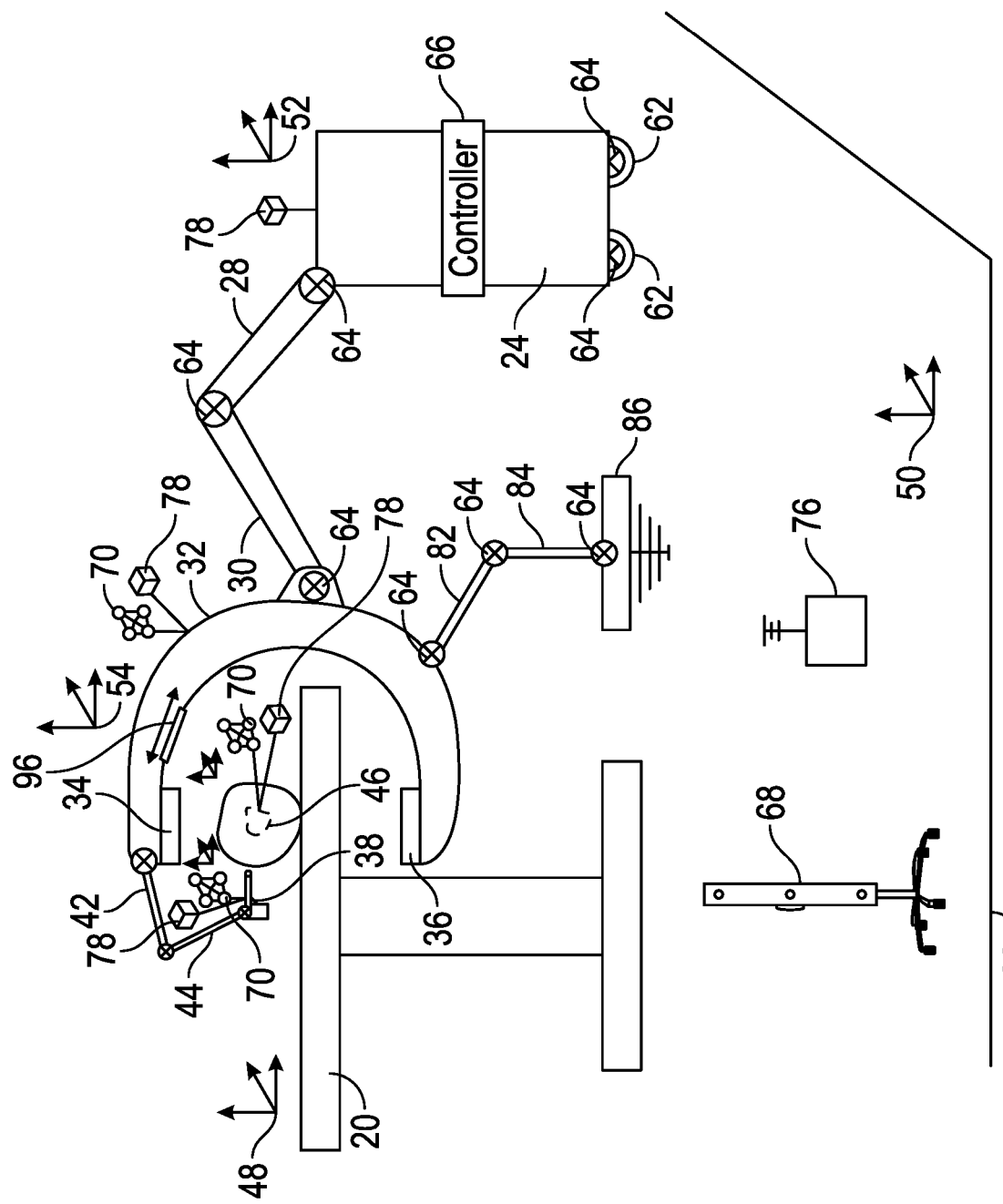
FIG. 3N depicts one embodiment of a robotic surgery system with integrated imaging capabilities.

Referring to FIGS. 3A-3N, various embodiments of systems for conducting robotic surgical procedures are presented, wherein interventional tools such as bone cutting instruments may be operated from a common platform also having integrated imaging capabilities to facilitate workflow optimization. Referring to FIG. 3A, conventionally one of the challenges in robotically-assisted interventional procedures has been registering surgical instrumentation with images that may be generated using imaging systems such as fluoroscopes, so that the instrumentation may be navigated around in a workspace relative to the imaged patient tissue structure with a high level of precision. As described above, this typically has required that a mobile imaging system and mobile robotic surgery system be given alternate access to the most immediate workspace around the targeted tissue structures—thus the workflow interruption for moving hardware, registering the coordinate systems of the various pieces of hardware relative to each other and the subject anatomy, and conducting portions of the imaging or surgical procedure serially. The system shown in FIG. 3A addresses this workflow challenge by integrating the interventional/surgical system with imaging technologies.

According to the embodiments herein, a geometric/mathematical relationship is established between the coordinate systems of various elements of the procedure, so that each of such elements may remain registered to the others. For example, referring again to FIG. 3A, a global coordinate system 50 is associated with the floor 22, ceiling, or walls of the operating room. Generally, the coordinate system 48 of the operating table 20 relative to the global coordinate system 50 will be known with an operating table fixedly attached to the floor 22 as shown. In one variation, the anatomy is temporarily immobilized relative to the operating table using straps or other mechanical coupling members. With the relationship between the coordinate system 58 of the targeted anatomy 46 and the coordinate system 48 of the operating table 20 known, an integrated imaging-intervention system may be registered to the operating table or anatomy, and with a knowledge of the position and/or orientation of various portions of such system, all associated coordinate systems and elements may be brought into inherent registration with the anatomy. In this way, imaging and surgical intervention, such as bone or other tissue cutting, may be accomplished with precision, along with simultaneous imaging. In one embodiment, a knowledge of the positions of one or more wheels 62 of a mobile base subsystem 24, along with the dimensions of such subsystem, is utilized to establish a transformation between the global coordinate system 50 and the coordinate system 52 for the mobile base 24. A first moveable support structure 26 includes a first member 28 movably coupled to a second member 30. The moveable support structure 26 is utilized to support and couple the mobile base 24 to a coupling member 32 configured to support two opposing imaging elements 34, 36 of a fluoroscopy system (i.e., wherein one element includes a source element and another element includes a detector element) in a known configuration relative to each other. In a preferred embodiment, whichever element is the detector element includes a flat panel detector. The flat panel detector may be an amorphous silicon panel detector. The flat panel detector may be a CMOS fluoroscopy panel. The flat panel detector may have an effective image area having a particular shape such as a circle, an ellipse, a square, or a rectangle. In one embodiment, a rectangular CMOS active fluoroscopy panel has dimensions of about 5 inches by about 6 inches. In a preferred embodiment, the corresponding source element includes an X-ray source. The source element may be configured to produce a collimated beam having a cross-sectional shape, such as a circle, an ellipse, a square, or a rectangle.

As shown in FIG. 3A, the coupling member 32 is also coupled to and configured to support a second moveable support structure 40 having a first member 42 movably coupled to a second member 44. The second member 44 is movably coupled to an instrument 38, such as a bone-cutting instrument. It is desirable to maintain a registration between all of the involved elements, and in particular the coordinate systems of the elements, including the coordinate system 58 of the targeted anatomy 46, the coordinate system 56 of the instrument 38, and the coordinate system 54 of imaging elements/coupling member 32 so that image-based intervention may be conducted.

One way of monitoring the relative positioning/orientation of various elements is to monitor and/or understand the positions of the various joints or moveable couplings 60 between the physical elements. For example, the first and the second moveable support structures may include joint rotation encoders and/or actuators at the moveable joints that may be read and/or controlled by a controller to electromechanically characterize movement of the elements of the system relative to each other. Alternatively, or in addition, the positions and/or orientations of the physical elements themselves may be monitored. FIGS. 3B-3F illustrate various embodiments wherein joint positions and/or physical element positions and/or orientations of an integrated imaging/intervention system are monitored, given a configuration wherein the targeted anatomy 46 is in a known fixed configuration relative to the coordinate systems of the operating table 48 and/or the operating room floor 50.

Referring to FIG. 3B, in one embodiment, moveable joints are fitted with joint encoders 64. The joint encoders 64 may be fitted to the moveable joints of one or more wheels 62 of the mobile base 24, to the moveable joints of the first moveable support structure 26, and to the moveable joints of the second moveable support structure 40. Each of these encoders 64 is operatively coupled (i.e., via wireless link or wired lead, not shown) back to a controller 66, such as a computer, which is coupled to the mobile base 24 as shown. Using the known geometric dimensions of the various physical elements, the encoder readings, and coordinate transformation techniques, the position and orientation of the instrument 38 relative to the anatomy 46, as well as the position and orientation of the imaging elements 34, 36 relative to the anatomy, may be determined in real or near-real time. The wheels 62 are configured to be manually or electromechanically lockable or braked to maintain position and orientation of the mobile base 24 relative to the floor 22.

Referring to FIG. 3C, an optical tracking system 68, along with a plurality of reflector arrays or sensors 70 fixedly or removably coupled to pertinent structures as shown, are also utilized to register such structures to the coordinate system 58 of the anatomy 46 if the relationship between the tracking system source/detector 68 and targeted anatomy 46 is established.

Referring to FIG. 3D, an electromagnetic tracking system 76, along with a plurality of electromagnetic sensors 78 fixedly or removably coupled to pertinent structures as shown (such sensors generally will be operatively coupled, via a system of wire leads (not shown) back to the source/detector 76 and/or back to a central controller 66. The source/detector 76 preferably also is operatively coupled to the controller 66, as shown with the depicted wire lead 74. The source/detector 76 is also utilized to register such structures to the coordinate system 58 of the anatomy 46 if the relationship between the tracking system source/detector 76 and targeted anatomy 46 is established.

Referring to FIG. 3E, a mechanical tracker subsystem 86 has one or more relatively stiff members 82, 84 intercoupled by encoded joints 64 is utilized to characterize the position and/or orientation of various elements of the system, such as the coupling member 32 as shown, relative to the floor 22 to which the mechanical tracker 86 is grounded or coupled. Encoded joints 64 for the second moveable support structure 40 are utilized to characterize the relationship between the coupling member 32 and the surgical instrument 38.

Referring to FIG. 3F, for illustrative purposes, it is shown that in some embodiments multiple tracking/characterization modalities (here encoded joints 64, optical tracking 68/70, electromechanical tracking 76/78, and mechanical tracking 64/86) are combined to understand the positioning and orientation of a surgical instrument 38, targeted anatomy 46, and imaging elements 34, 36 relative to each other.

Referring to FIGS. 3G-3J, such tracking configurations may further be employed to monitor the position and/or orientation of the anatomy relative to other elements and coordinate systems. For example, referring to FIG. 3G, a combination of joint encoders 64 and optical tracking 68/70 are utilized to characterize the positioning and/or orientation of the anatomy 46, surgical instrument 38, and imaging elements 34, 36.

Referring to FIG. 3H, a combination of joint encoders 64 and electromagnetic tracking 76/78 are utilized to characterize the positioning and/or orientation of the anatomy 46, surgical instrument 38, and imaging elements 34, 36.

Referring to FIG. 3I, there is shown a combination of joint encoders 64 on portions of the system elements, along with a mechanical tracker 94 having additional joint encoders 64 coupled directly to the anatomy 46 on one end and coupled to the operating table 20 at the other end. This combination also may be utilized to characterize the positioning and/or orientation of the anatomy 46, surgical instrument 38, and imaging elements 34, 36.

Referring to FIG. 3J, a combination of joint encoders 64, electromagnetic tracking 76/78, mechanical tracking 86/64, and optical tracking 68/70 are utilized to characterize the positioning and/or orientation of the anatomy 46, surgical instrument 38, and imaging elements 34, 36.

Referring to FIG. 3K, a combination of joint encoders 64 and optical tracking (utilizing emitter/detector 96 and reflector array 70) are utilized to characterize the positioning and/or orientation of the anatomy 46, surgical instrumentation 38, and imaging elements 34, 36, here with the optical tracker emitter/detector 96 directly coupled to one element (such as coupling member 32) of the integrated system. In the depicted embodiment, the emitter/detector 96 is movably controlled by a user interface to move as depicted by arrow 98. Preferably, the emitter/detector 96 is electromechanically moveable using an actuator controlled by a user interface.

Referring to FIG. 3L, a combination of joint encoders 64 and electromagnetic tracking 76/78) are utilized to characterize the positioning and/or orientation of the anatomy 46, surgical instrumentation 38, and imaging elements 34, 36. In the embodiment shown, the electromagnetic transmitter 76 is mounted upon the coupling member 32, or may be mounted to another structure of the integrated system.

Referring to FIG. 3M, a combination of joint encoders 64 coupled to the system elements and an encoded mechanical tracker (having arms 88, 90, 92 and joint encoders 64) are utilized to characterize the positioning and/or orientation of the anatomy 46, surgical instrumentation 38, and imaging elements 34, 36. In the embodiment shown, the mechanical tracker (having arms 88, 90, and 92 and encoders 64) is coupled to the coupling member 32 or other structure of the integrated system. Also shown in this embodiment is a lockable linkage having one or more substantially rigid elongate members 104, 106 and one or more releasably lockable joints 108. The lockable linkage is configured to temporarily fix and structurally couple the operating table 20 and the coupling member 32, to serve as a stress/load relief for the integrated system, and to minimize micromotion that may occur from deflection/strain of components under relatively large cantilevered loads.

For illustrative purposes, a multi-modality configuration is shown in FIG. 3N, with encoded joints 64 coupled to the system elements, a mechanical tracker 86 having encoded joints 64, electromagnetic sensing/tracking 76/78, optical sensing/tracking 68/70, and optical tracking utilizing an emitter/detector 96 coupled to an element of the system and reflector array 70 combined to characterize the positioning and/or orientation of the anatomy 46, surgical instrumentation 38, and imaging elements 34, 36.

Figure 4A:
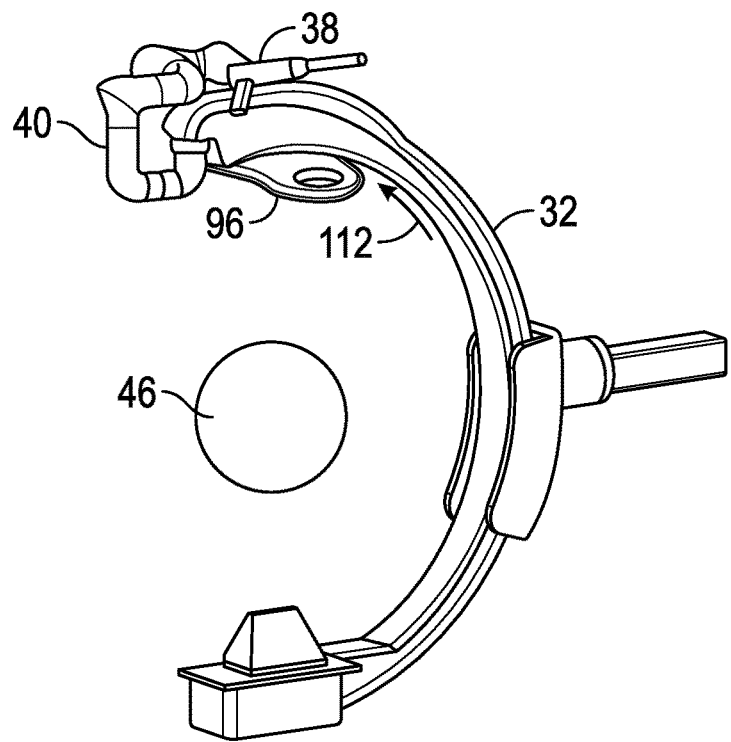
FIG. 4A depicts portions of one embodiment of a robotic surgery system with integrated imaging capabilities, wherein a moveable instrument support structure is configured to be temporarily positioned away from one or more imaging elements during imaging.
Figure 4B:
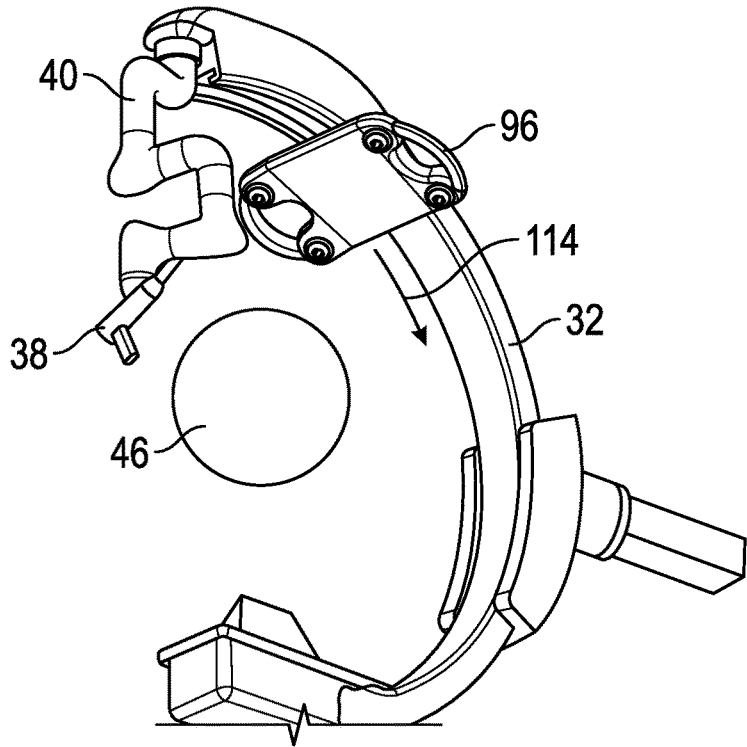
FIG. 4B depicts portions of one embodiment of a robotic surgery system with integrated imaging capabilities, wherein an imaging element is temporarily re-positioned during a procedure with an instrument.

Referring to FIGS. 4A-4B, the second moveable support structure 40 is configured to automatically move, or be moveable, such that the surgical instrument 38 is mobilized out of the way of the imaging element or tracking hardware 96. The imaging element 96 may then be moved, as depicted by arrow 112, into a position nearby. Upon completion of a discrete imaging or tracking exercise or acquisition, the imaging element or tracking hardware 96 may be moved back, as depicted by arrow 114, into an away position to accommodate more movement workspace for the second moveable support structure 40 and instrument 38.

Figure 5:
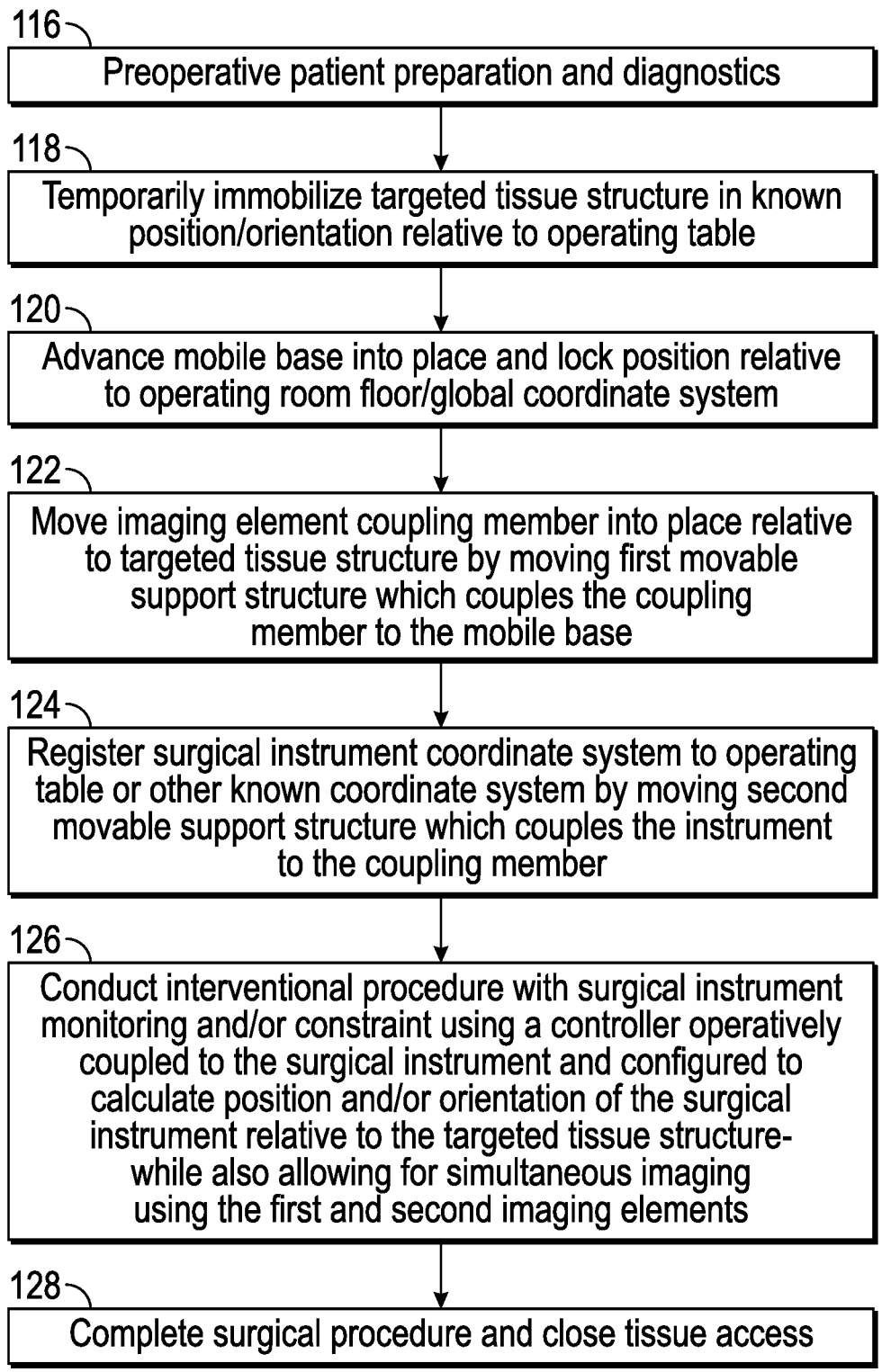
FIG. 5 illustrates one embodiment of a procedure for utilizing an embodiment of a robotic surgery system with integrated imaging capabilities.
Figure 6:
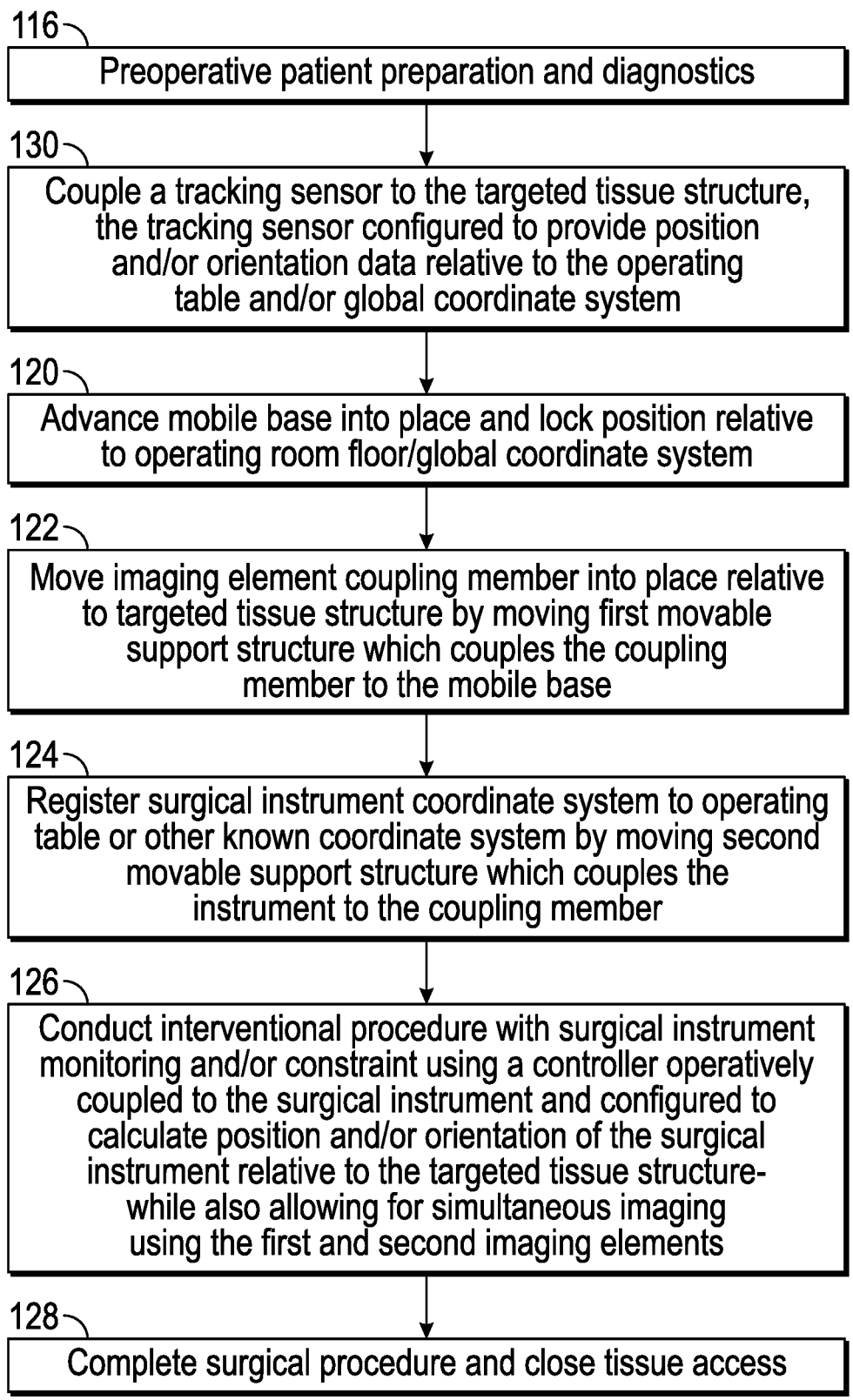
FIG. 6 illustrates one embodiment of a procedure for utilizing an embodiment of a robotic surgery system with integrated imaging capabilities.
Figure 7:
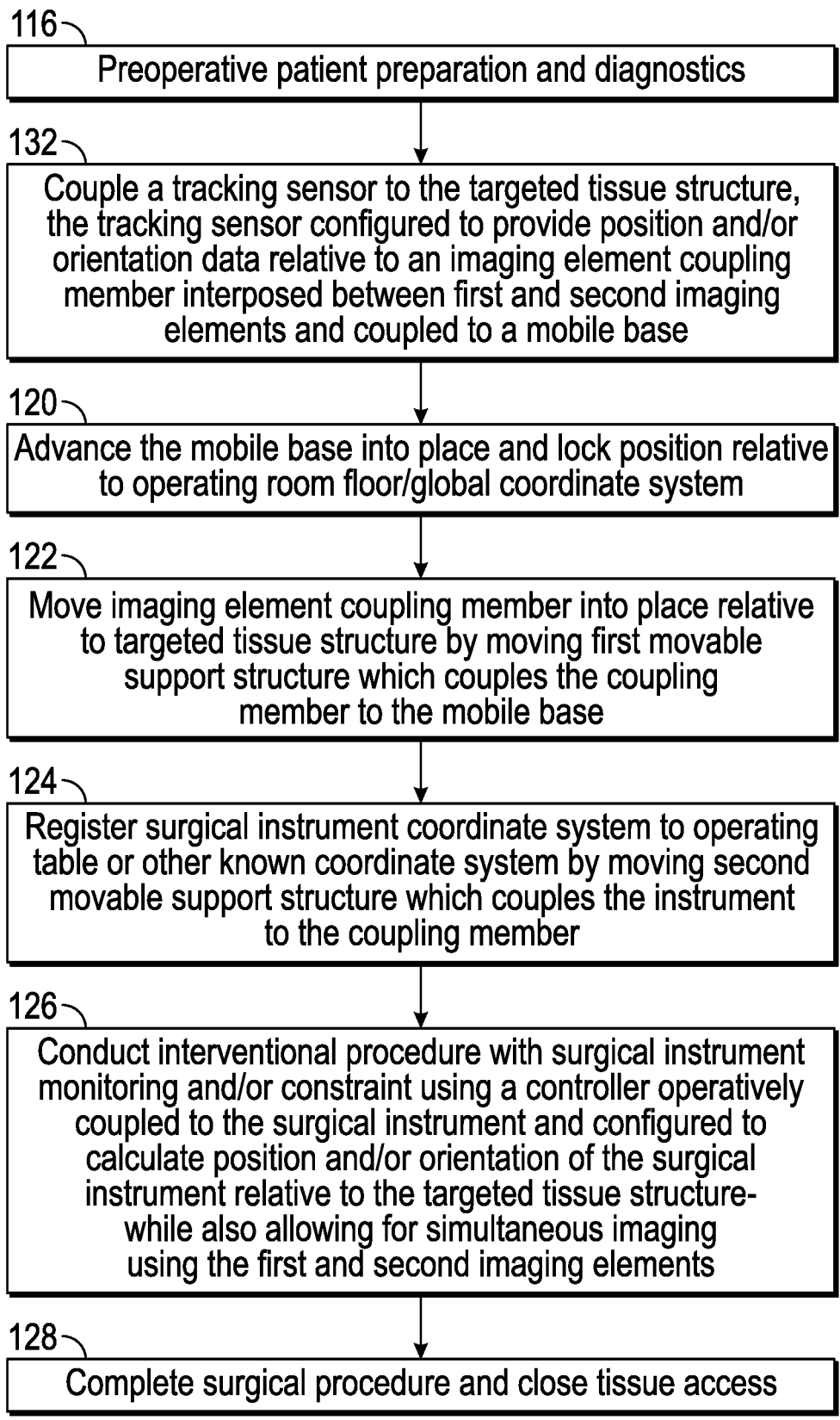
FIG. 7 illustrates one embodiment of a procedure for utilizing an embodiment of a robotic surgery system with integrated imaging capabilities.

Referring to FIGS. 5-7, techniques for utilizing systems such as those depicted in FIGS. 3A-4B are illustrated.

Referring to FIG. 5, after preoperative patient preparation and diagnostics (step 116), the targeted tissue structure, such as a bone or joint of an appendage, is temporarily immobilized relative to the operating table (step 118). A mobile base of an integrated imaging/intervention system is advanced into place and locked into position relative to the operating room floor using locking wheels (step 120). An imaging element coupling member is moved into place relative to the targeted tissue structure by moving first moveable support structure which couples the coupling member to the mobile base (step 122). A surgical instrument is then moved into place to have a workspace suitable for the intervention on the tissue structure using first and second moveable support structures coupled by a coupling member, and the surgical instrument is registered to a known coordinate system (step 124). Intervention is conducted while also allowing for simultaneous imaging using the inherently registered imaging components (step 126), after which the procedure is completed and tissue access closed (step 128).

Referring to FIG. 6, an embodiment similar to that of FIG. 5 is illustrated, with the exception that at least one tracking sensor (for example, an encoded mechanical tracker, an electromagnetic sensor, an optical sensor, etc.) is coupled directly to the targeted tissue structure (step 130), for example, as described above in reference to FIGS. 3G-3J, to characterize the position and/or orientation of the tissue relative to another known coordinate system. In this exemplary technique, after preoperative patient preparation and diagnostics (step 116), a tracking sensor is coupled to the targeted tissue structure (step 130). The tracking sensor is configured to provide position and/or orientation date relative to the operative table and/or global coordinate system. A mobile base of an integrated imaging/intervention system is advanced into place and locked into position relative to the operating room floor using locking wheels (step 120). An imaging element coupling member is moved into place relative to the targeted tissue structure by moving first moveable support structure which couples the coupling member to the mobile base (step 122). A surgical instrument is then moved into place to have a workspace suitable for the intervention on the tissue structure using first and second moveable support structures coupled by a coupling member, and the surgical instrument is registered to a known coordinate system (step 124). Intervention is conducted while also allowing for simultaneous imaging using the inherently registered imaging components (step 126), after which the procedure is completed and tissue access closed (step 128).

Referring to FIG. 7, an embodiment similar to that of FIG. 5 is illustrated, with the exception that at least one tracking sensor (for example, an encoded mechanical tracker, an electromagnetic sensor, an optical sensor, etc.) is intercoupled between the targeted tissue structure and a portion of the integrated intervention/imaging hardware itself (step 132), for example, as described above in reference to FIGS. 3K-3N, to characterize the position and/or orientation of the tissue relative to another known coordinate system. In this exemplary technique, after preoperative patient preparation and diagnostics (step 116), a tracking sensor is coupled to the targeted tissue structure (step 132). The tracking sensor is configured to provide position and/or orientation date relative to an imaging element coupling member interposed between first and second imaging elements, and coupled to a mobile base. A mobile base of an integrated imaging/intervention system is advanced into place and locked into position relative to the operating room floor using locking wheels (step 120). An imaging element coupling member is moved into place relative to the targeted tissue structure by moving first moveable support structure which couples the coupling member to the mobile base (step 122). A surgical instrument is then moved into place to have a workspace suitable for the intervention on the tissue structure using first and second moveable support structures coupled by a coupling member, and the surgical instrument is registered to a known coordinate system (step 124). Intervention is conducted while also allowing for simultaneous imaging using the inherently registered imaging components (step 126), after which the procedure is completed and tissue access closed (step 128).

Figure 8A:
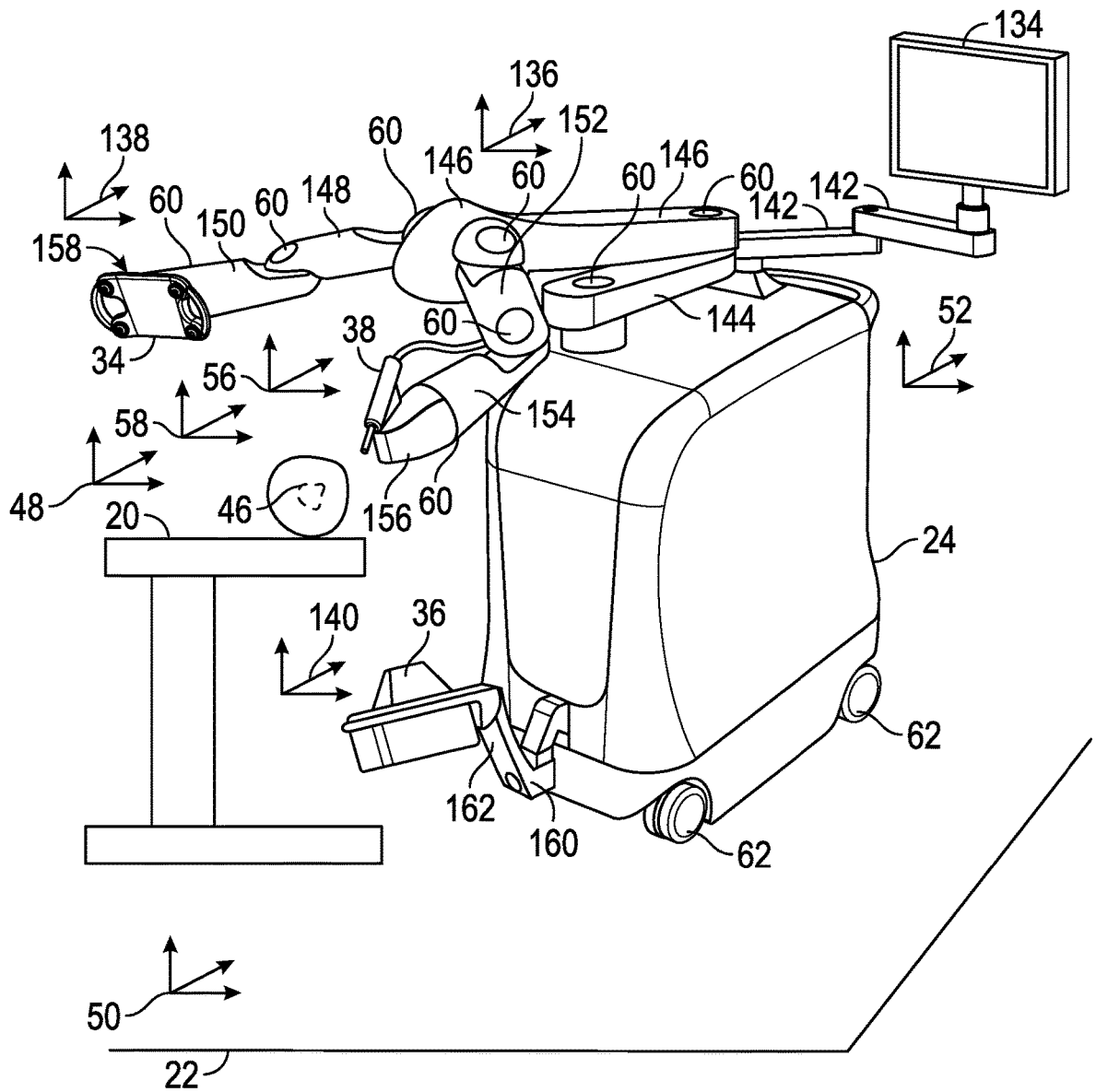
FIG. 8A depicts one embodiment of a robotic surgery system with integrated imaging capabilities.

Referring to FIGS. 8A-11, another group of embodiments is depicted wherein a three-armed configuration may be utilized for integrated imaging/intervention, with some similarity to the imaging, sensing, registration paradigms discussed above in reference to FIGS. 3A-7. Referring to FIG. 8A, a mobile base 24 including a controller (not shown; similar to controller 66 shown in FIGS. 3B-3N) and lockable wheels 62 function as a central mechanical hub for three arms, as well as for a display 134 and display support 142. Various sensing, monitor, and mechanical configurations may be utilized, with an objective of having various coordinate systems and components registered so that imaging and interventional steps may be conducted with an efficient workflow, along with inherent registration given available sensing and geometric dimensions. The configuration of FIG. 8A features two imaging elements opposed from each other with the targeted tissue structure 46 in between, mounted upon or coupled to an operating table 20 that is mounted to or coupled to the floor 22 of the operating room. One imaging element 36 (either a source or a detector) is coupled to a lower robotic arm having two elongate segments 160, 162, while the other element 34 (the other of either a source or a detector) is coupled to a right upper robotic arm having two elongate segments 148, 150 coupled by joints 60. A one or more degree-of-freedom wrist 158 (not visible) may provide additional freedom of motion between the imaging element 34 and the end of the most distal right upper robotic arm segment 150. In this embodiment, a left upper robotic arm also has two segments 152, 154 joined by joints 60 is utilized to move/navigate a surgical instrument 38 using a wrist component 156 which may have multiple degrees of freedom, such as yaw, pitch, and roll. Both upper arms in the depicted configuration are coupled to a first common arm member 146, which is movably coupled to a second common arm member 144, which is movably coupled to the mobile base 24. As described below, the coordinate systems of the various components, such as the coordinate systems of the first common arm member (coordinate system 136), first imaging element (coordinate system 138), second imaging element (coordinate system 140), targeted tissue structure (coordinate system 58), surgical instrument (coordinate system 56), mobile base (coordinate system 52), and operating room (coordinate system 50) may all be kept in registration with appropriate monitoring of positions and/or orientations of the various components given certain variables such as geometric dimensions.

Figure 8B:
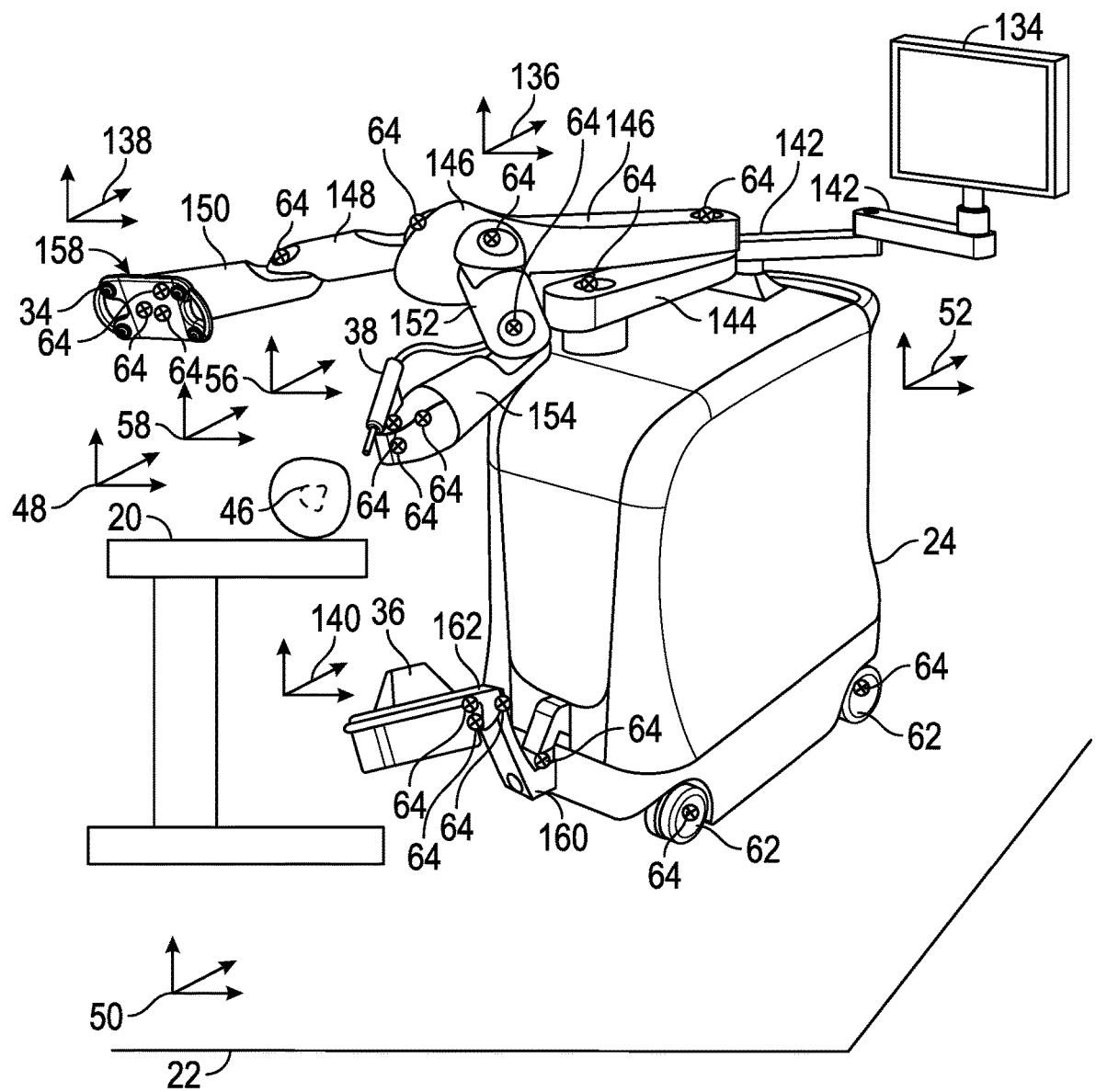
FIG. 8B depicts one embodiment of a robotic surgery system with integrated imaging capabilities.

Referring to FIG. 8B, encoded joints 64 are utilized to maintain registration between the various components of the system relative to each other. Given a relationship to a coordinate system 58 of the targeted tissue structure 46 (which may be temporarily fixed relative to the operating table 20), the surgical instrumentation 38, anatomy 46, and imaging elements 34, 36 may be kept in registration for the procedure.

Figure 8C:
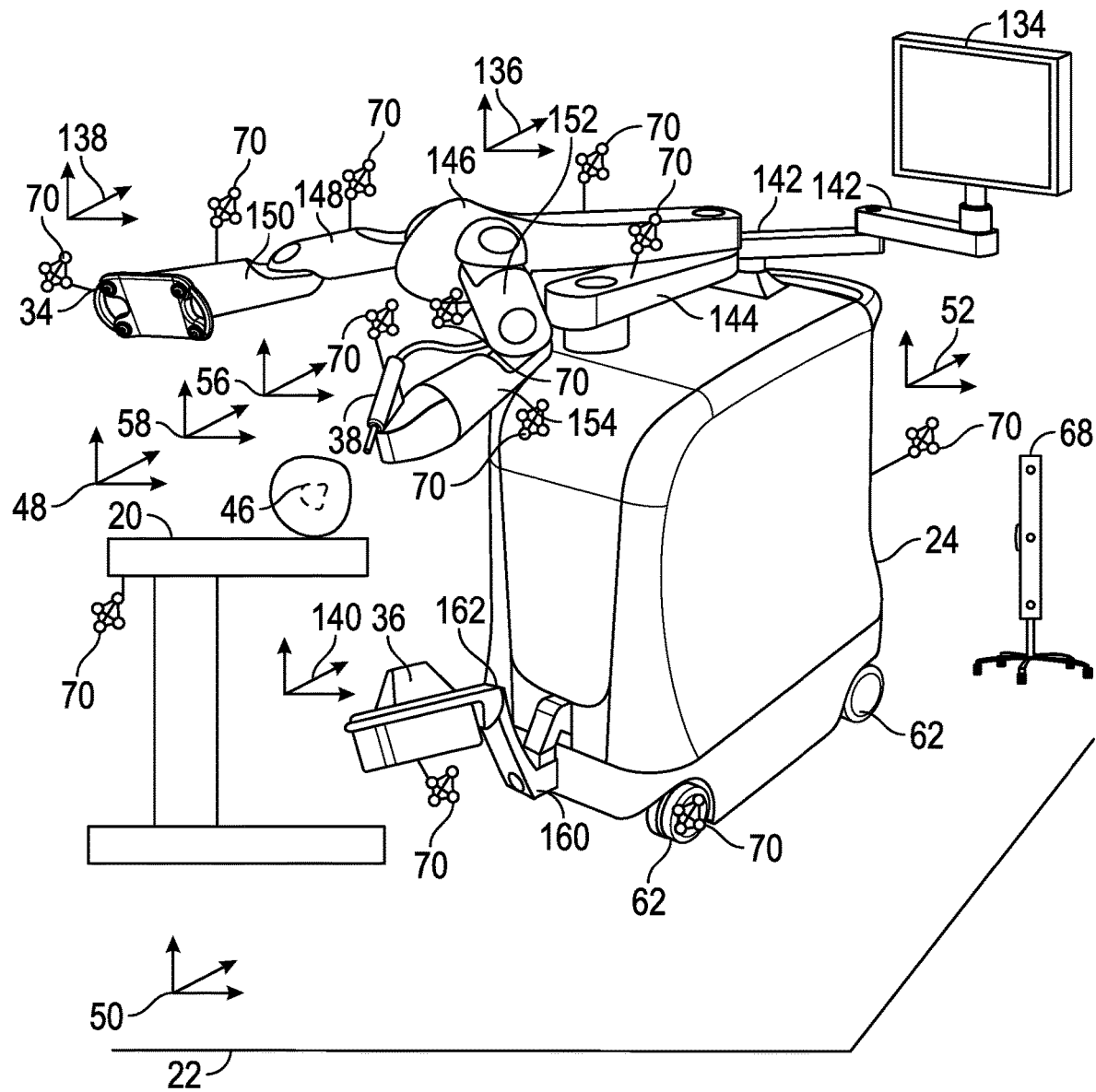
FIG. 8C depicts one embodiment of a robotic surgery system with integrated imaging capabilities.

Referring to FIG. 8C, optical tracking sensors 70 and an optical tracking emitter/detector 68 and a plurality of reflector arrays or sensors 70 fixedly or removably coupled to pertinent structures are utilized to monitor the positions and/or orientations of the various components, as opposed to encoded joints as in the embodiment of FIG. 8B.

Figure 8D:
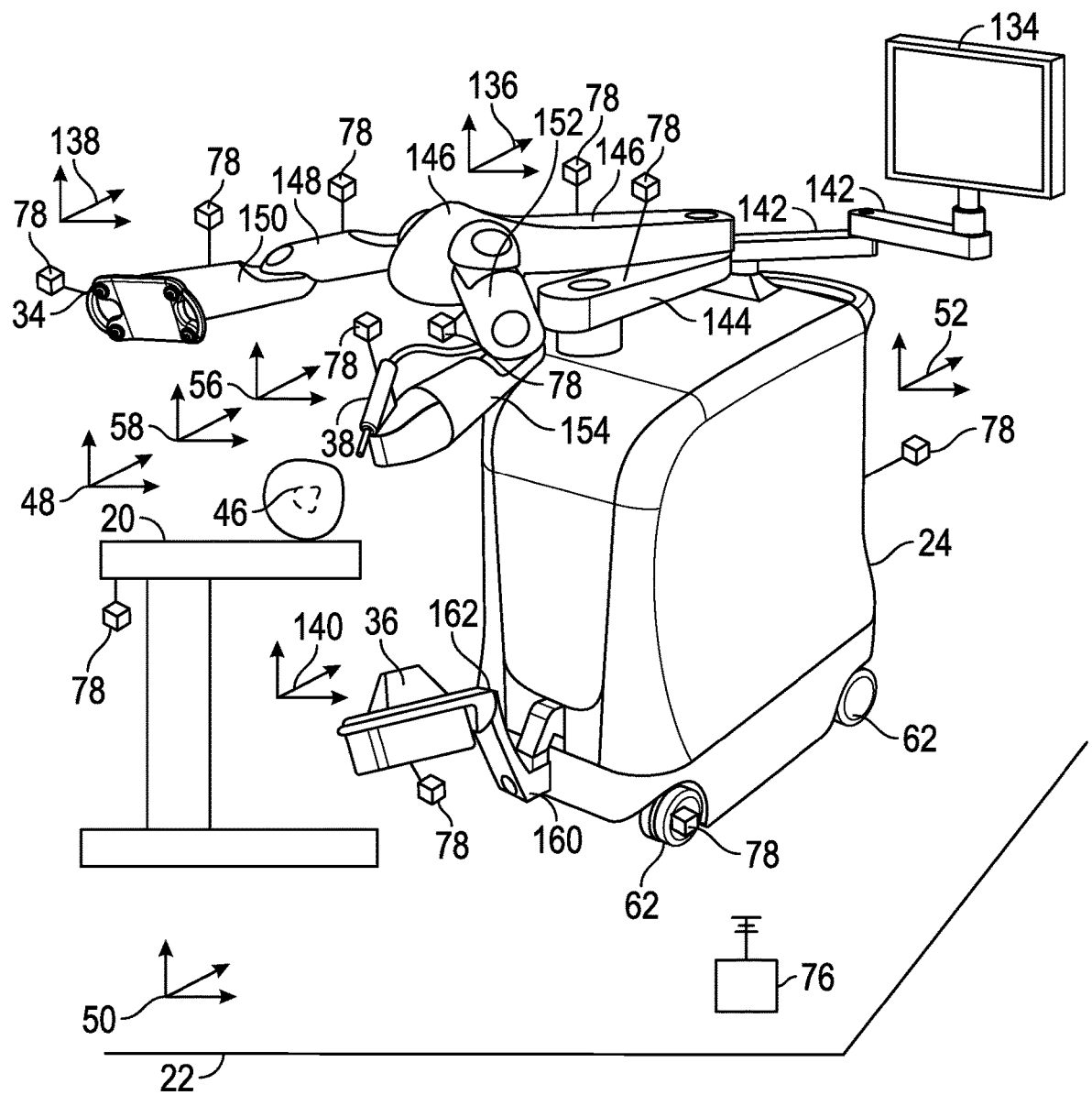
FIG. 8D depicts one embodiment of a robotic surgery system with integrated imaging capabilities.

Referring to FIG. 8D, electromagnetic tracking sensors 78 and an optical tracking emitter/system 76 are utilized to monitor the positions and/or orientations of the various components, as opposed to encoded joints as in the embodiment of FIG. 8B.

Figure 8E:
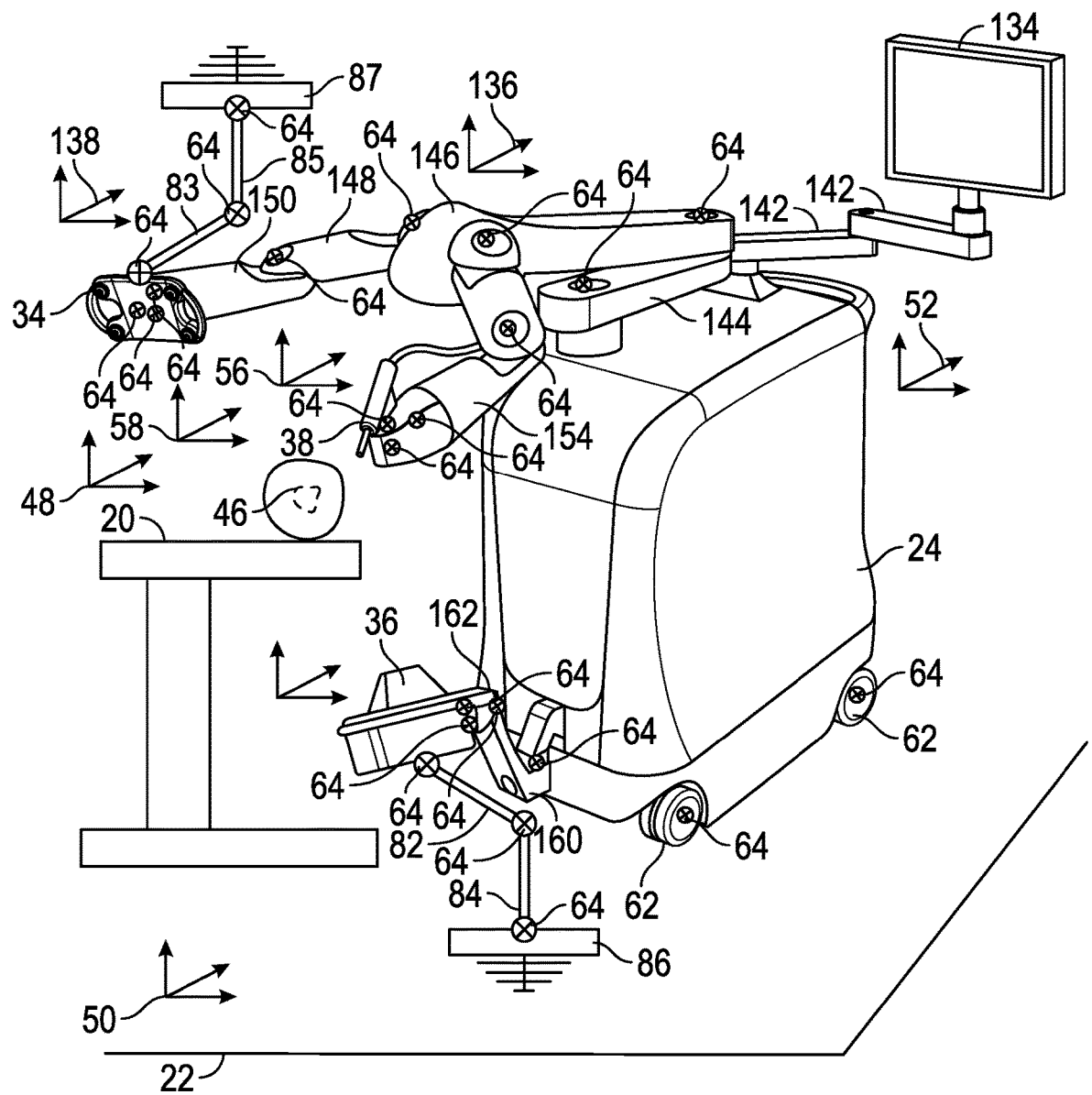
FIG. 8E depicts one embodiment of a robotic surgery system with integrated imaging capabilities.

Referring to FIG. 8E, a combination of encoded joints 64 and mechanical trackers 83/85/87, 82/84/86 having encoded joints 64 are utilized to monitor the positions and/or orientations of the various components.

Figure 8F:
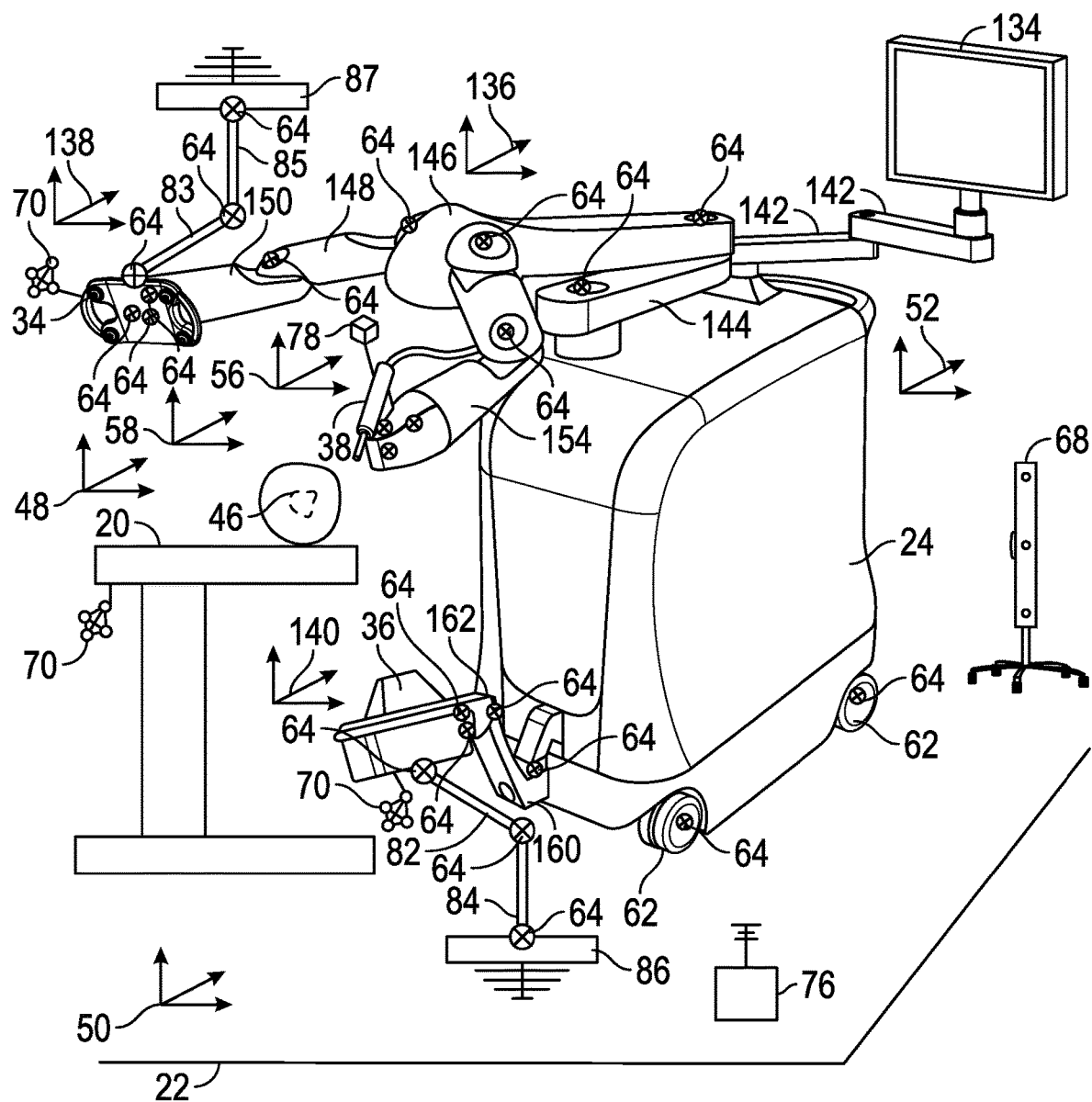
FIG. 8F depicts one embodiment of a robotic surgery system with integrated imaging capabilities.

Referring to FIG. 8F, a system combining multiple monitoring modalities, such as optical tracking 68/70, electromagnetic tracking 76/78, encoded joints 64, and additional mechanical trackers 83/85/87, 82/84/86 with encoded joints 64 are utilized to monitor the positions and/or orientations of the various components.

Figure 8G:
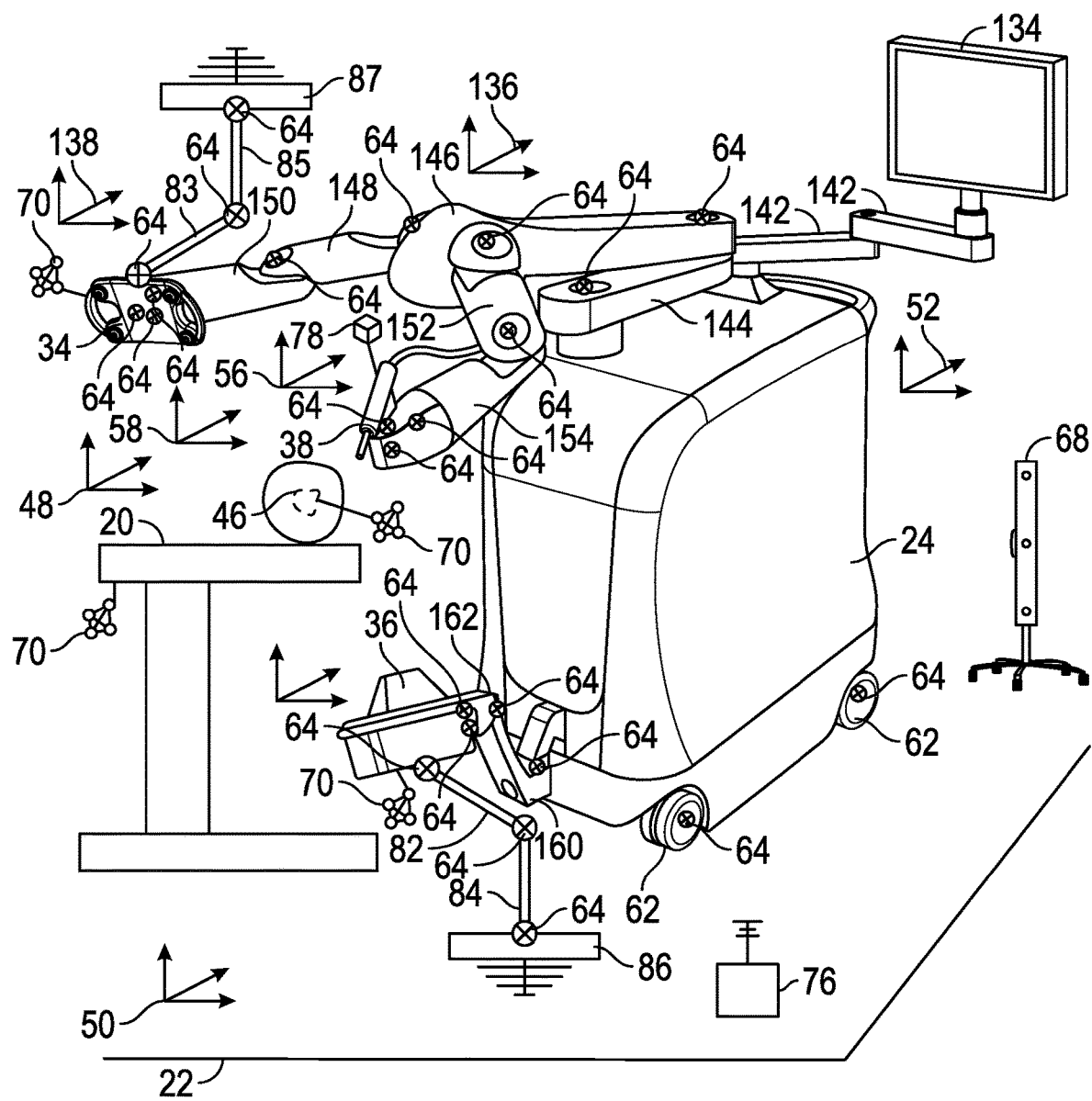
FIG. 8G depicts one embodiment of a robotic surgery system with integrated imaging capabilities.
Figure 8H:
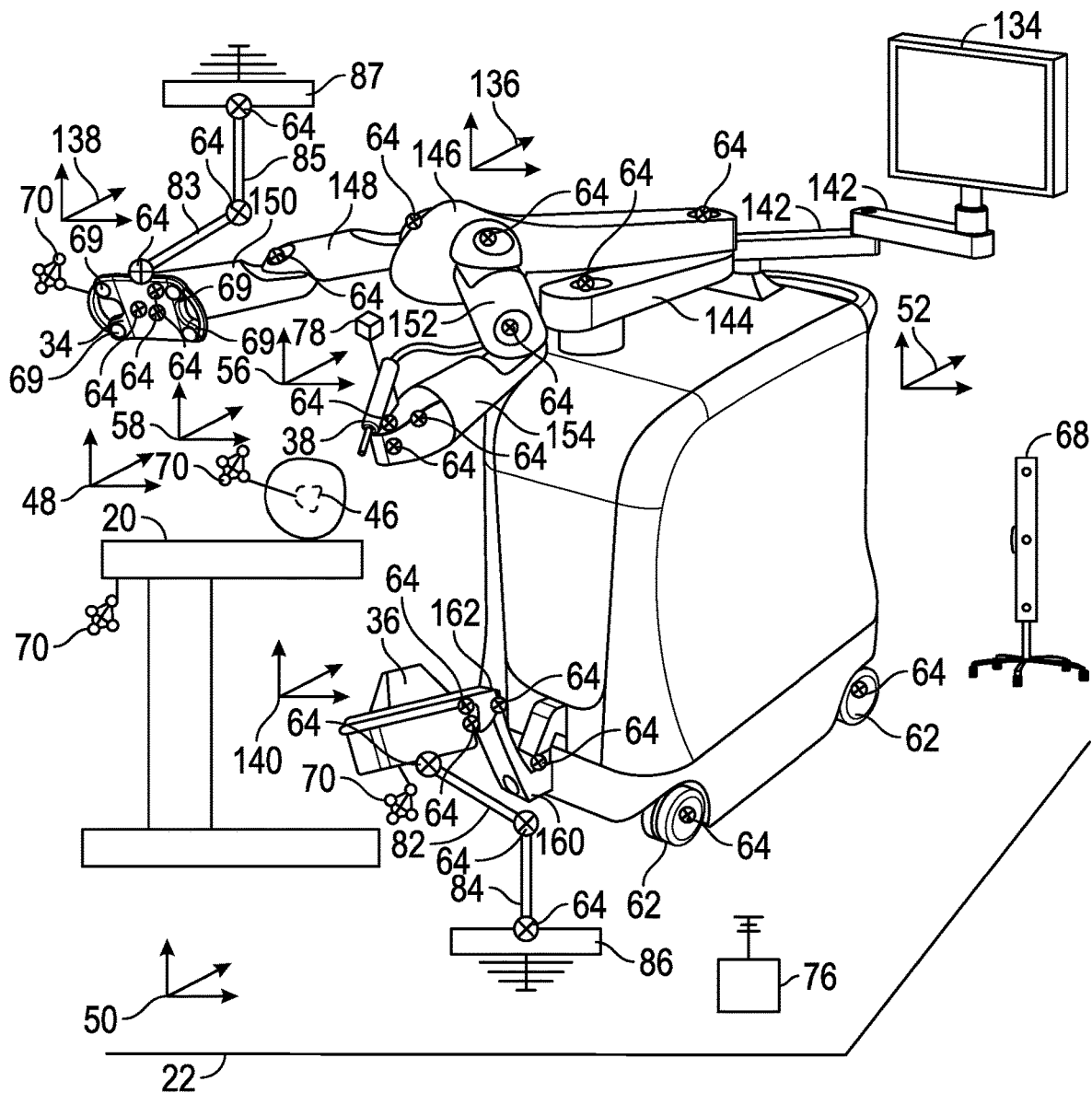
FIG. 8H depicts one embodiment of a robotic surgery system with integrated imaging capabilities.

FIGS. 8G and 8H feature embodiments similar to that of FIG. 8F, with the exception that tracking configurations are also utilized to track the anatomy itself. FIG. 8G depicts optical tracking 68/70 with the emitter/detector 68 external to the operational system hardware. FIG. 8H depicts the emitter detector 69 integral with the system, i.e., having a portion of the hardware, such as imaging element 34 as shown, mounted upon one of the arms. An external emitter/detector 68 is also shown, and may also be utilized in parallel.

Figure 9:
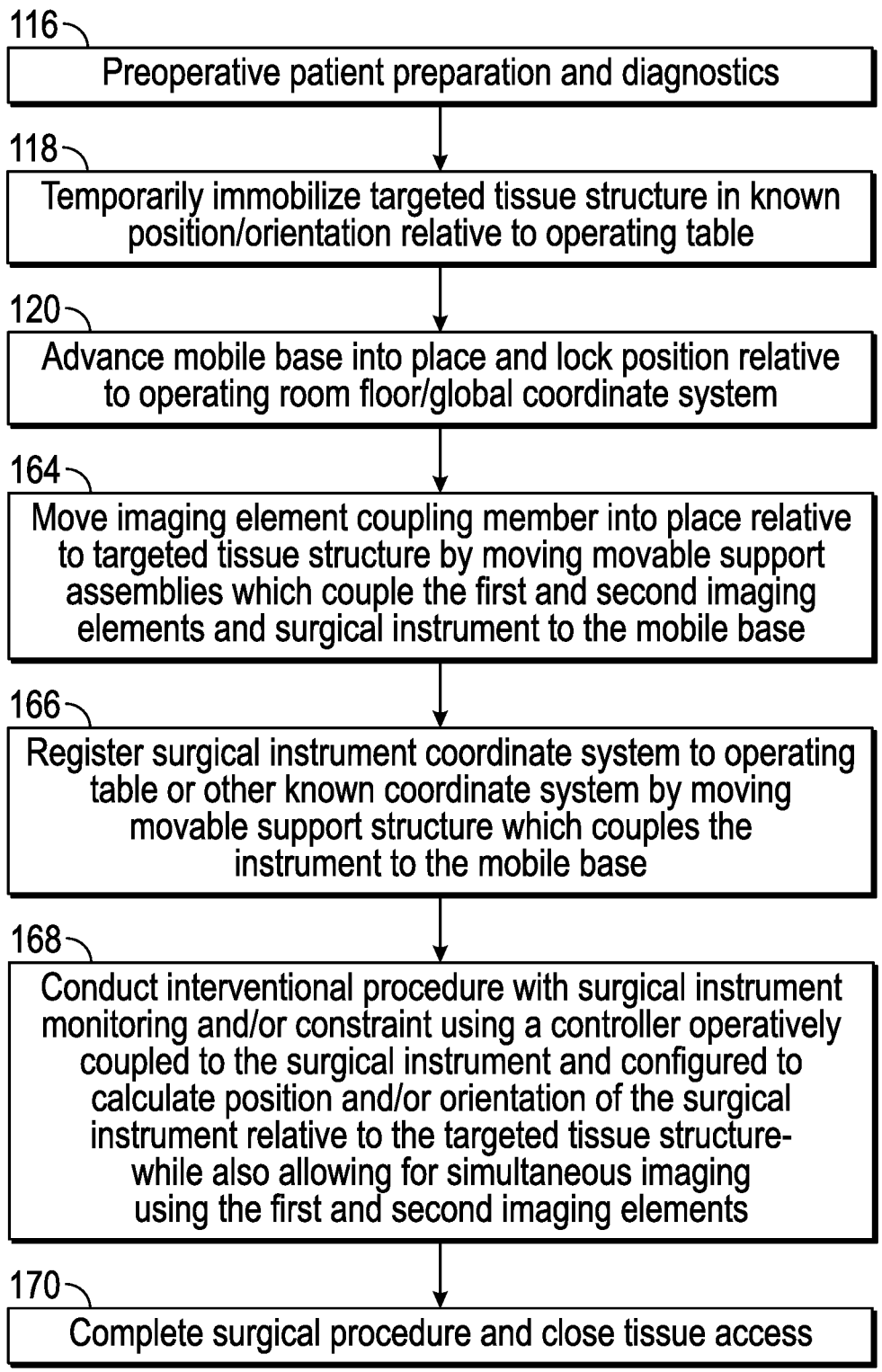
FIG. 9 illustrates one embodiment of a procedure for utilizing an embodiment of a robotic surgery system with integrated imaging capabilities.
Figure 10:
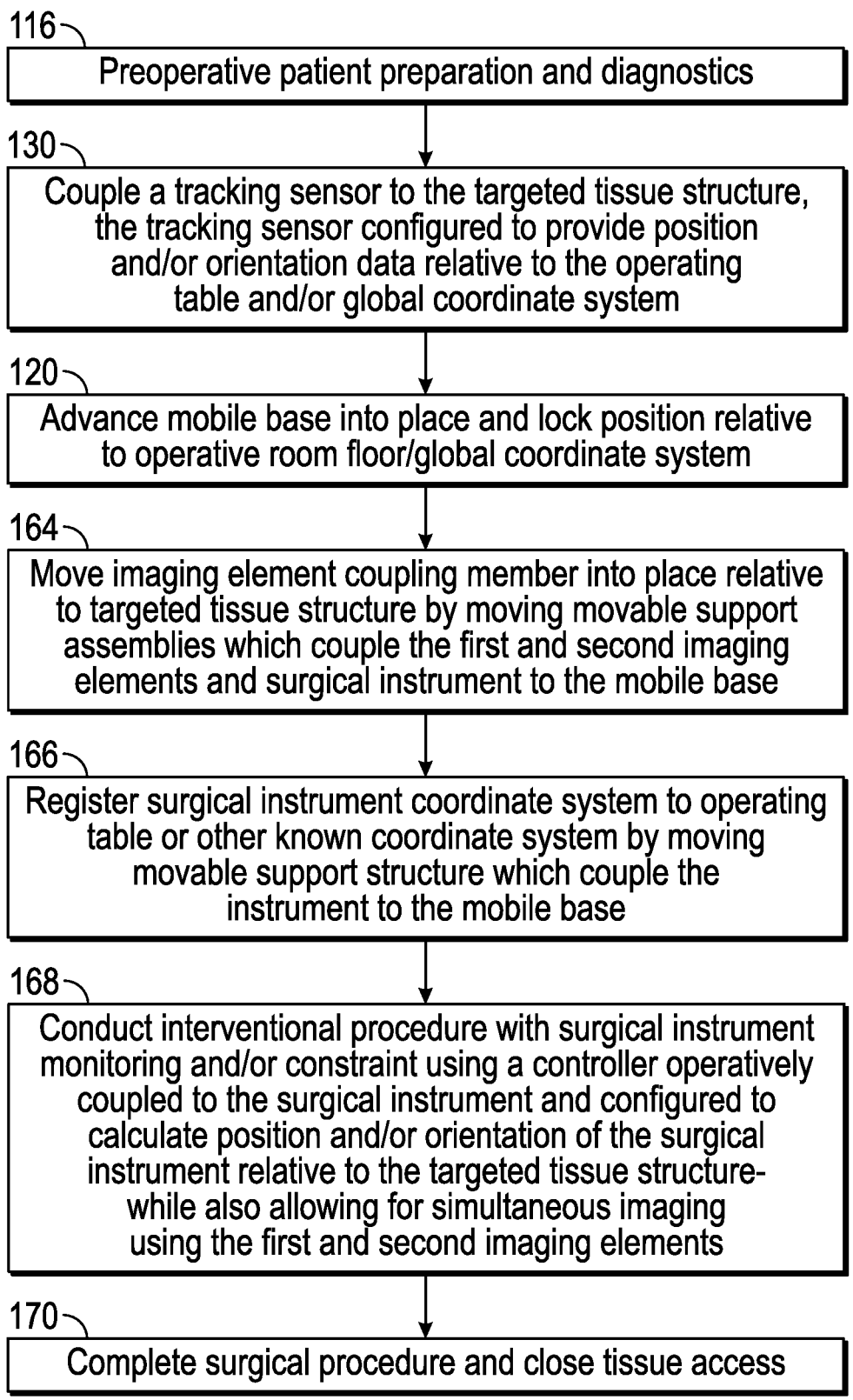
FIG. 10 illustrates one embodiment of a procedure for utilizing an embodiment of a robotic surgery system with integrated imaging capabilities.
Figure 11:
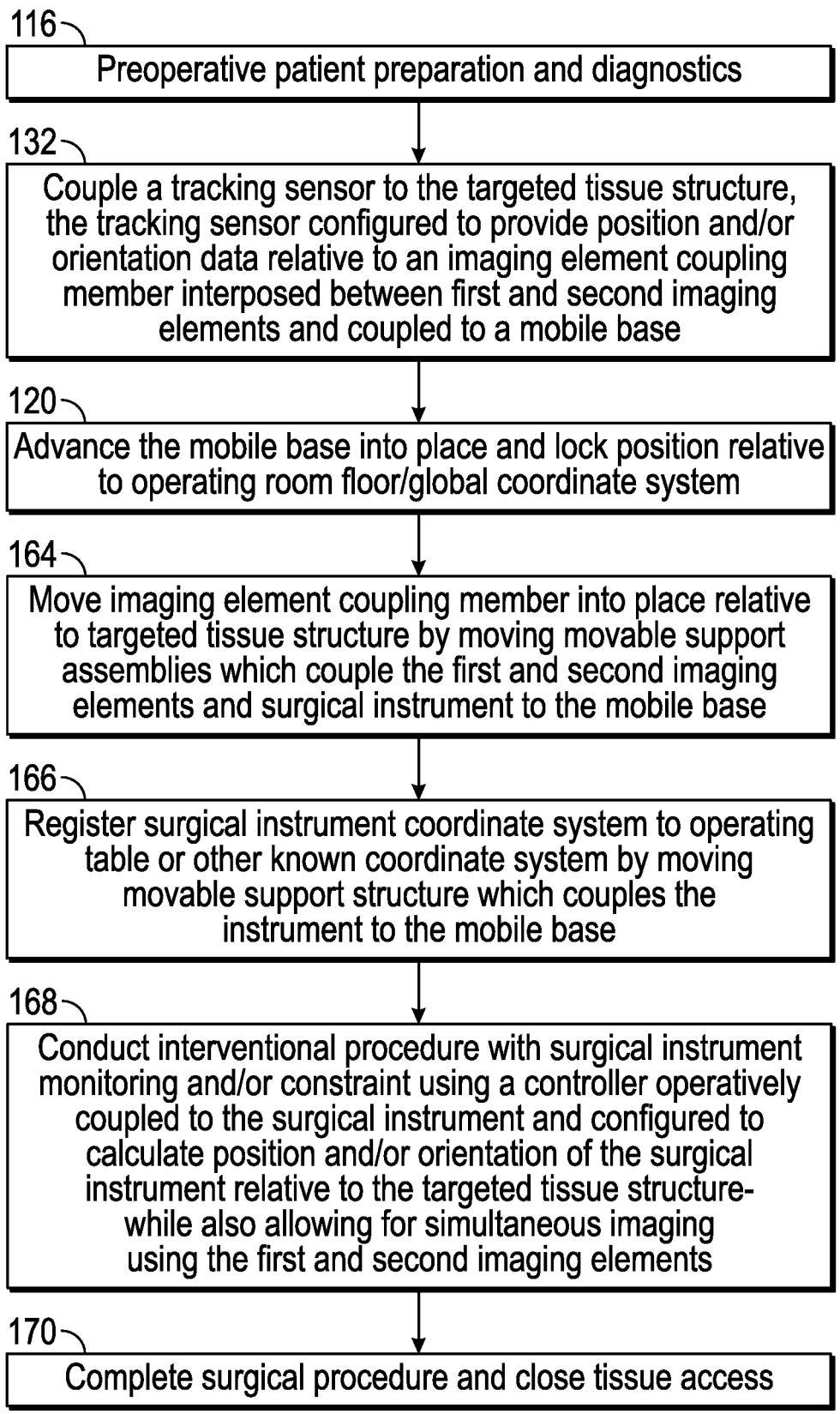
FIG. 11 illustrates one embodiment of a procedure for utilizing an embodiment of a robotic surgery system with integrated imaging capabilities.

Referring to FIGS. 9-11, techniques for utilizing systems such as those depicted in FIGS. 8A-8H are illustrated.

Referring to FIG. 9, after preoperative patient preparation and diagnostics (step 116), in one embodiment the targeted tissue structure, such as a bone or joint of an appendage, is temporarily immobilized relative to the operating table (step 118). A mobile base of an integrated imaging/intervention system is advanced into place and locked into position relative to the operating room floor using locking wheels (step 120). An imaging element coupling member is moved into place relative to the targeted tissue structure by moving moveable support assemblies which couple the first and second imaging elements and surgical instrument to the mobile base (step 164). A surgical instrument is then moved into place to have a workspace suitable for the intervention on the tissue structure using the moveable support structure coupled to the base, and the surgical instrument is registered to a known coordinate system (step 166). Intervention is conducted while also allowing for simultaneous imaging using the inherently registered imaging components (step 168), after which the procedure is completed and tissue access closed (step 170).

Referring to FIG. 10, an embodiment similar to that of FIG. 9 is illustrated, with the exception that at least one tracking sensor (for example, an encoded mechanical tracker, an electromagnetic sensor, an optical sensor, etc.) is coupled directly to the targeted tissue structure (step 130), for example, as described above in reference to FIG. 8G, to characterize the position and/or orientation of the tissue relative to another known coordinate system. In this exemplary technique, after preoperative patient preparation and diagnostics (step 116), a tracking sensor is coupled to the targeted tissue structure (step 130). The tracking sensor is configured to provide position and/or orientation date relative to the operative table and/or global coordinate system. A mobile base of an integrated imaging/intervention system is advanced into place and locked into position relative to the operating room floor using locking wheels (step 120). An imaging element coupling member is moved into place relative to the targeted tissue structure by moving moveable support assemblies which couple the first and second imaging elements and surgical instrument to the mobile base (step 164). A surgical instrument is then moved into place to have a workspace suitable for the intervention on the tissue structure using the moveable support structure coupled to the base, and the surgical instrument is registered to a known coordinate system (step 166). Intervention is conducted while also allowing for simultaneous imaging using the inherently registered imaging components (step 168), after which the procedure is completed and tissue access closed (step 170).

Referring to FIG. 11, an embodiment similar to that of FIG. 9 is illustrated, with the exception that at least one tracking sensor (for example, an encoded mechanical tracker, an electromagnetic sensor, an optical sensor, etc.) is intercoupled between the targeted tissue structure and a portion of the integrated intervention/imaging hardware itself (step 132), for example, as described above in reference to FIG. 8H, to characterize the position and/or orientation of the tissue relative to another known coordinate system. In this exemplary embodiment, after preoperative patient preparation and diagnostics (step 116), a tracking sensor is coupled to the targeted tissue structure (step 132). The tracking sensor is configured to provide position and/or orientation date relative to an imaging element coupling member interposed between first and second imaging elements, and coupled to a mobile base. A mobile base of an integrated imaging/intervention system is advanced into place and locked into position relative to the operating room floor using locking wheels (step 120). An imaging element coupling member is moved into place relative to the targeted tissue structure by moving moveable support assemblies which couple the first and second imaging elements and surgical instrument to the mobile base (step 164). A surgical instrument is then moved into place to have a workspace suitable for the intervention on the tissue structure using the moveable support structure coupled to the base, and the surgical instrument is registered to a known coordinate system (step 166). Intervention is conducted while also allowing for simultaneous imaging using the inherently registered imaging components (step 168), after which the procedure is completed and tissue access closed (step 170).

Figure 12A:
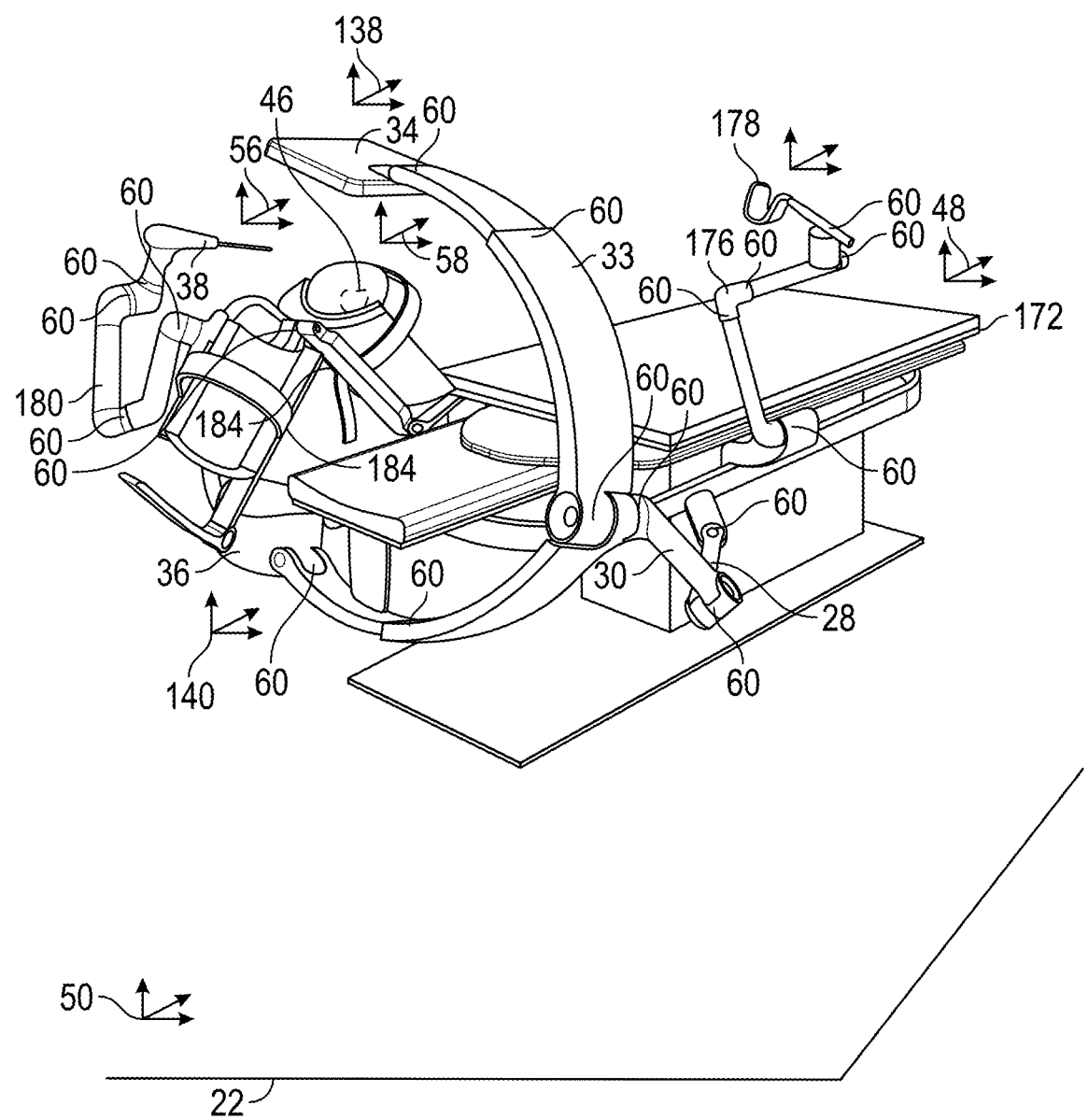
FIG. 12A depicts one embodiment of a robotic surgery system with integrated imaging capabilities.

Referring to FIGS. 12A-15, another group of embodiments is depicted wherein a operating table-based configuration may be utilized for integrated imaging/intervention, with some similarity to the imaging, sensing, registration paradigms discussed above in reference to FIGS. 3A-7. Referring to FIG. 12A, the operating table 172 is optionally temporarily or permanently fixedly coupled to the floor 22. The table 172 is fixed particularly in embodiments wherein a coordinate system of an external element, such as an optical tracking emitter/detector, is utilized, and thus movement of that coordinate system relative to the table is of additional importance. The table 172 functions as a central mechanical hub for an imaging arm structure having elements 28, 30, 33, an anatomy support structure 184, and an instrument support structure 180 mounted or coupled to the anatomy support structure 184. Various sensing, monitor, and mechanical configurations may be utilized, with an objective of having various coordinate systems and components registered so that imaging and interventional steps may be conducted with an efficient workflow, along with inherent registration given available sensing and geometric dimensions. The configuration of FIG. 12A features two imaging elements 34, 36 opposed from each other with the targeted tissue structure 46 in between, mounted upon or coupled to the operating table 172 by virtue of the anatomy support structure 184. One imaging element 36 (either a source or a detector) is coupled to a lower portion of the coupling member 33 while the other element 34 (the other of either a source or a detector) is coupled to an upper aspect of the coupling member 33. moveable joints 60 preferably are utilized to couple more rigid components in positions of desired freedom of motion, as in the embodiments described above. An auxiliary stabilization structure or arm 176 featuring a stabilization interface member 178 may also be movably coupled to the operating table 172. As described below, the coordinate systems of the various components, such as the coordinate systems of the first imaging element (coordinate system 138), second imaging element (coordinate system 140), targeted tissue structure (coordinate system 58), surgical instrument (coordinate system 56), operating table (coordinate system 48), and operating room (coordinate system 50) may all be kept in registration with appropriate monitoring of positions and/or orientations of the various components given certain variables such as geometric dimensions.

Figure 12B:
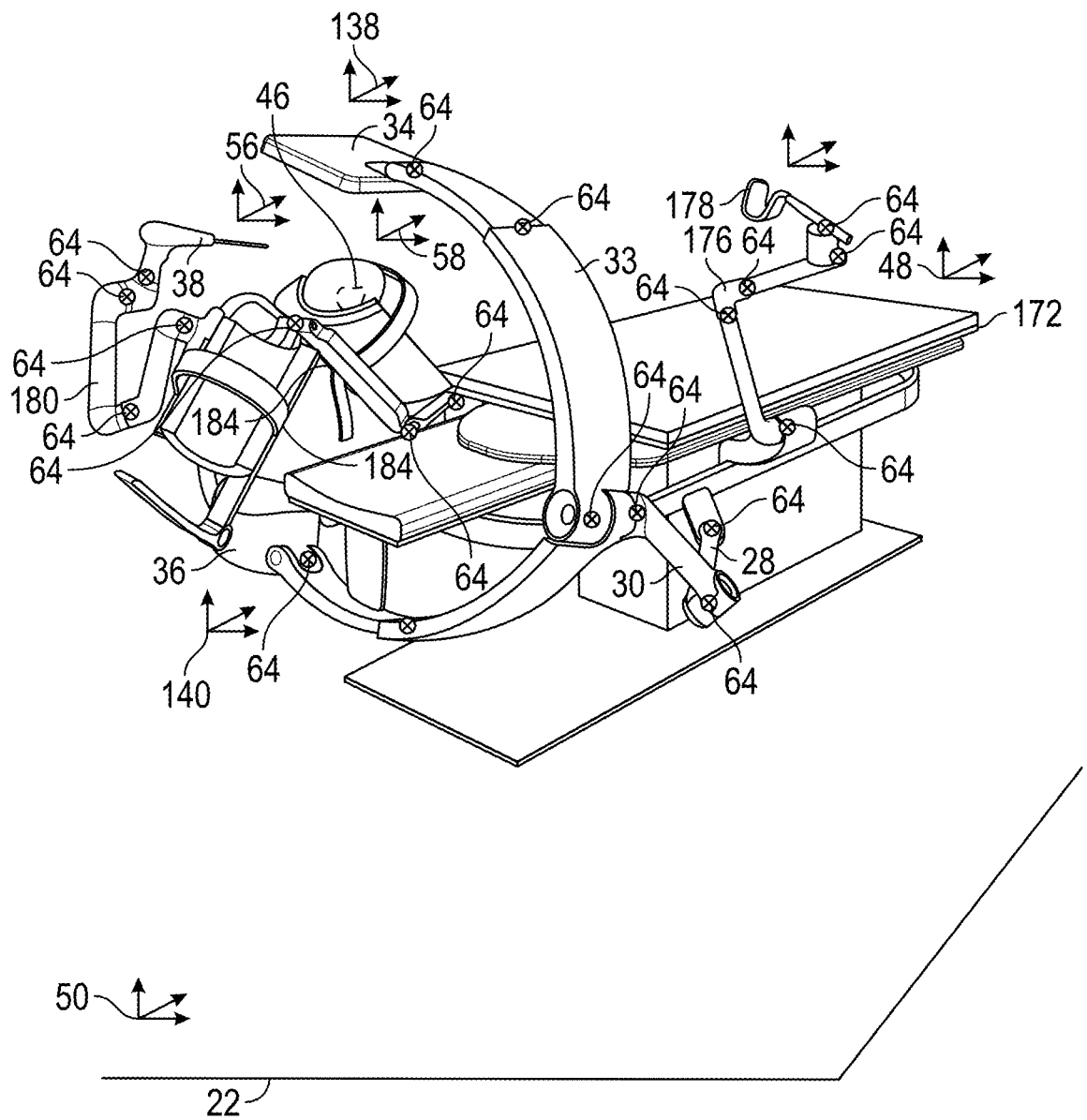
FIG. 12B depicts one embodiment of a robotic surgery system with integrated imaging capabilities.

Referring to FIG. 12B, encoded joints 64 are utilized to maintain registration between the various components of the system relative to each other. Given a relationship to a coordinate system 58 of the targeted tissue structure 46 (which may be temporarily fixed relative to the operating table 172), the surgical instrumentation 38, anatomy 46, and imaging elements 34, 36 may be kept in registration for the procedure.

Figure 12C:
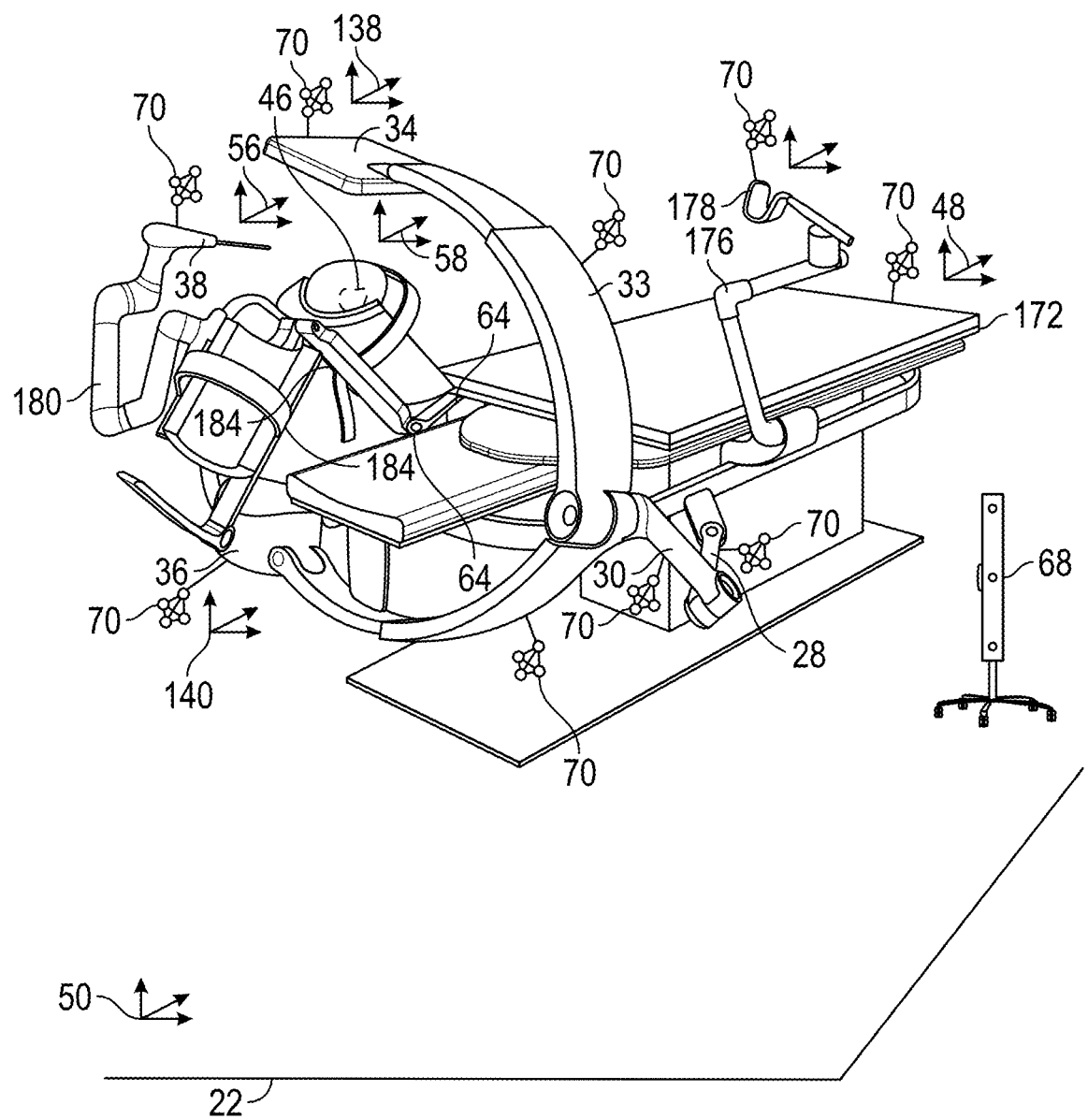
FIG. 12C depicts one embodiment of a robotic surgery system with integrated imaging capabilities.

Referring to FIG. 12C, optical tracking sensors 70 and an optical tracking emitter/detector 68 are utilized to monitor the positions and/or orientations of the various components, as opposed to encoded joints as in the embodiment of FIG. 12B.

Figure 12D:
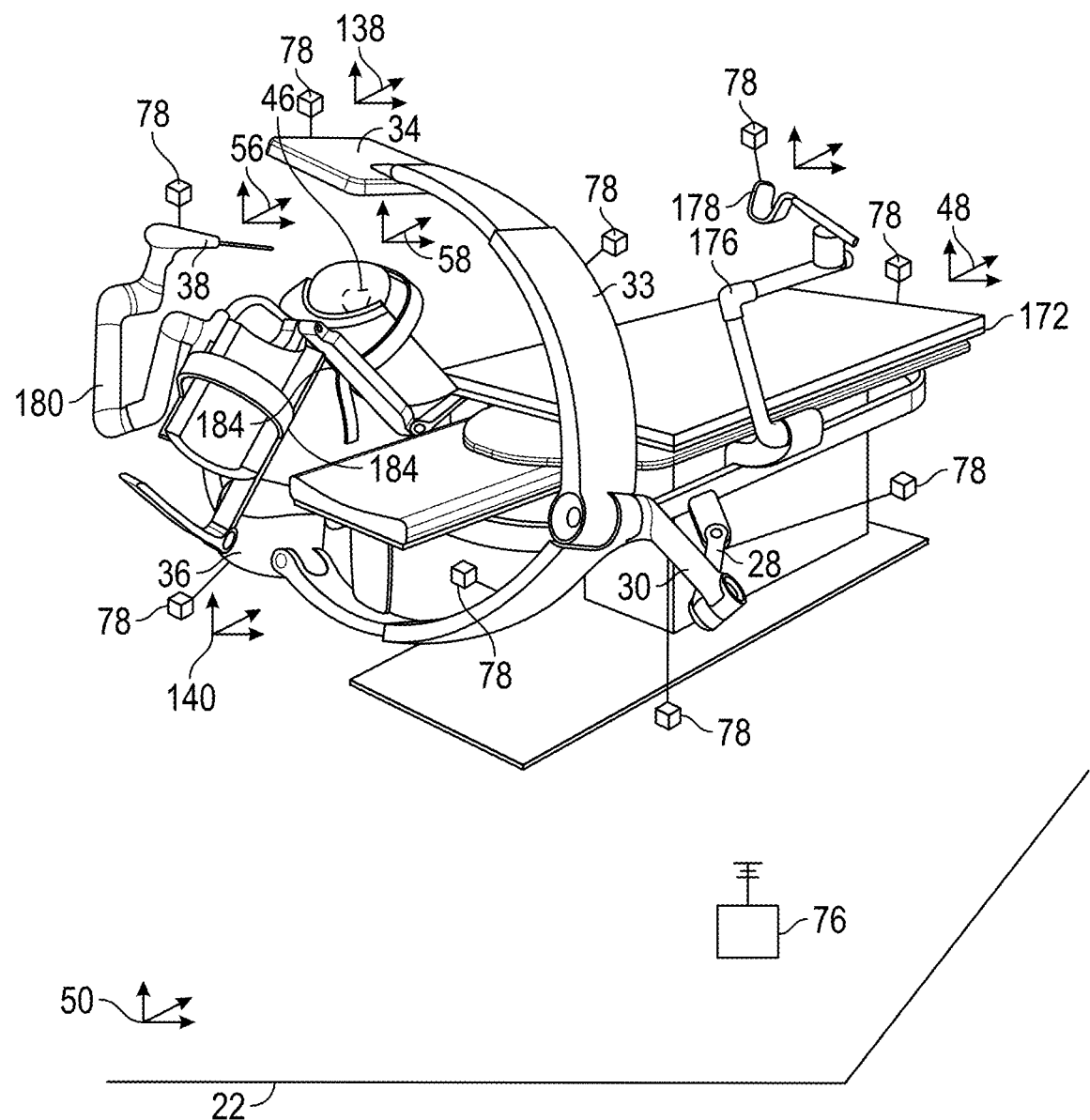
FIG. 12D depicts one embodiment of a robotic surgery system with integrated imaging capabilities.

Referring to FIG. 12D, electromagnetic tracking sensors 78 and an optical tracking emitter/system 76 are utilized to monitor the positions and/or orientations of the various components, as opposed to encoded joints as in the embodiment of FIG. 12B.

Figure 12E:
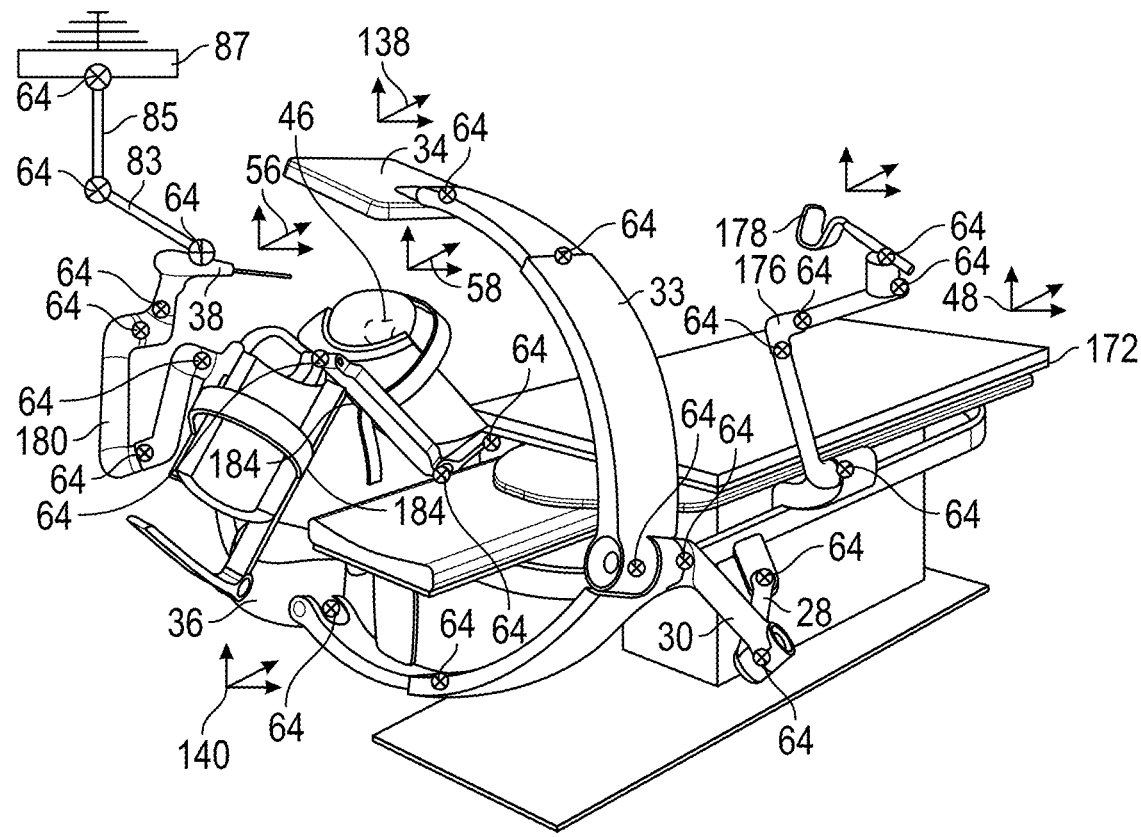
FIG. 12E depicts one embodiment of a robotic surgery system with integrated imaging capabilities.

Referring to FIG. 12E, a combination of encoded joints 64 and mechanical tracker 83/85/87 having encoded joints 64 are utilized to monitor the positions and/or orientations of the various components.

Figure 12F:
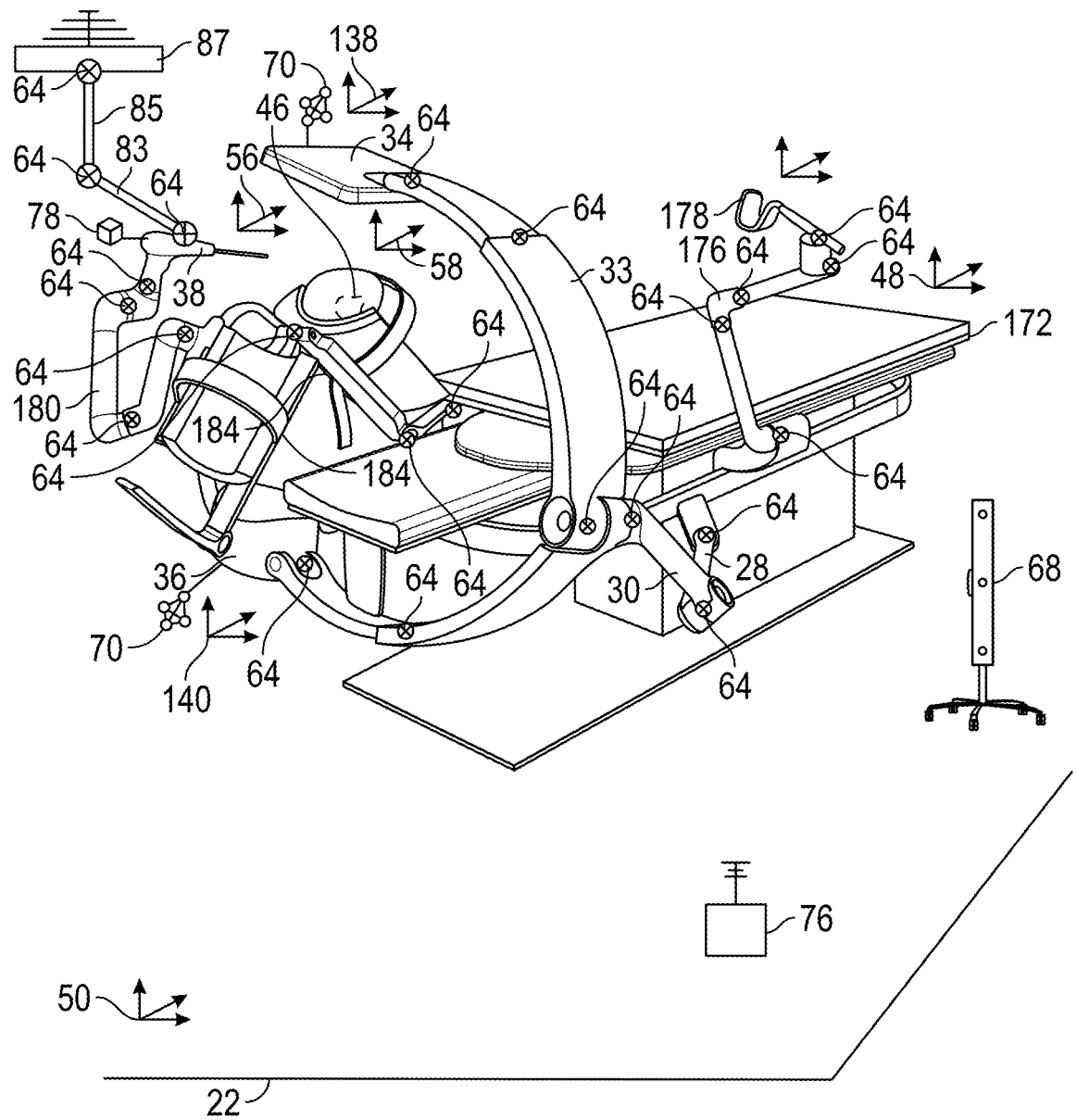
FIG. 12F depicts one embodiment of a robotic surgery system with integrated imaging capabilities.

Referring to FIG. 12F, a system combining multiple monitoring modalities, such as optical tracking 68/70, electromagnetic tracking 76/78, encoded joints 64, and additional mechanical tracker 83/85/87 with encoded joints 64 are utilized to monitor the positions and/or orientations of the various components.

Figure 12G:
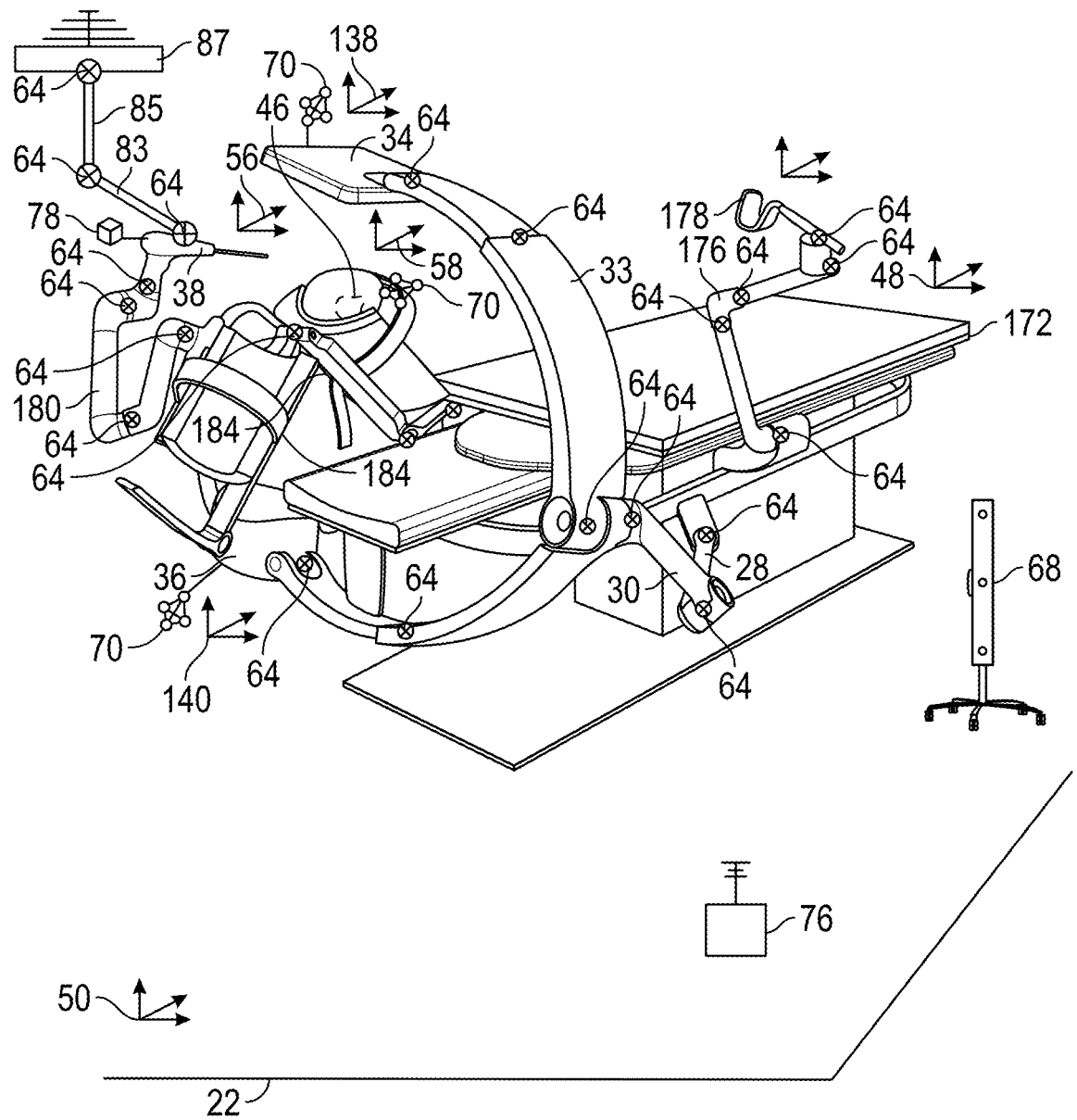
FIG. 12G depicts one embodiment of a robotic surgery system with integrated imaging capabilities.
Figure 12H:
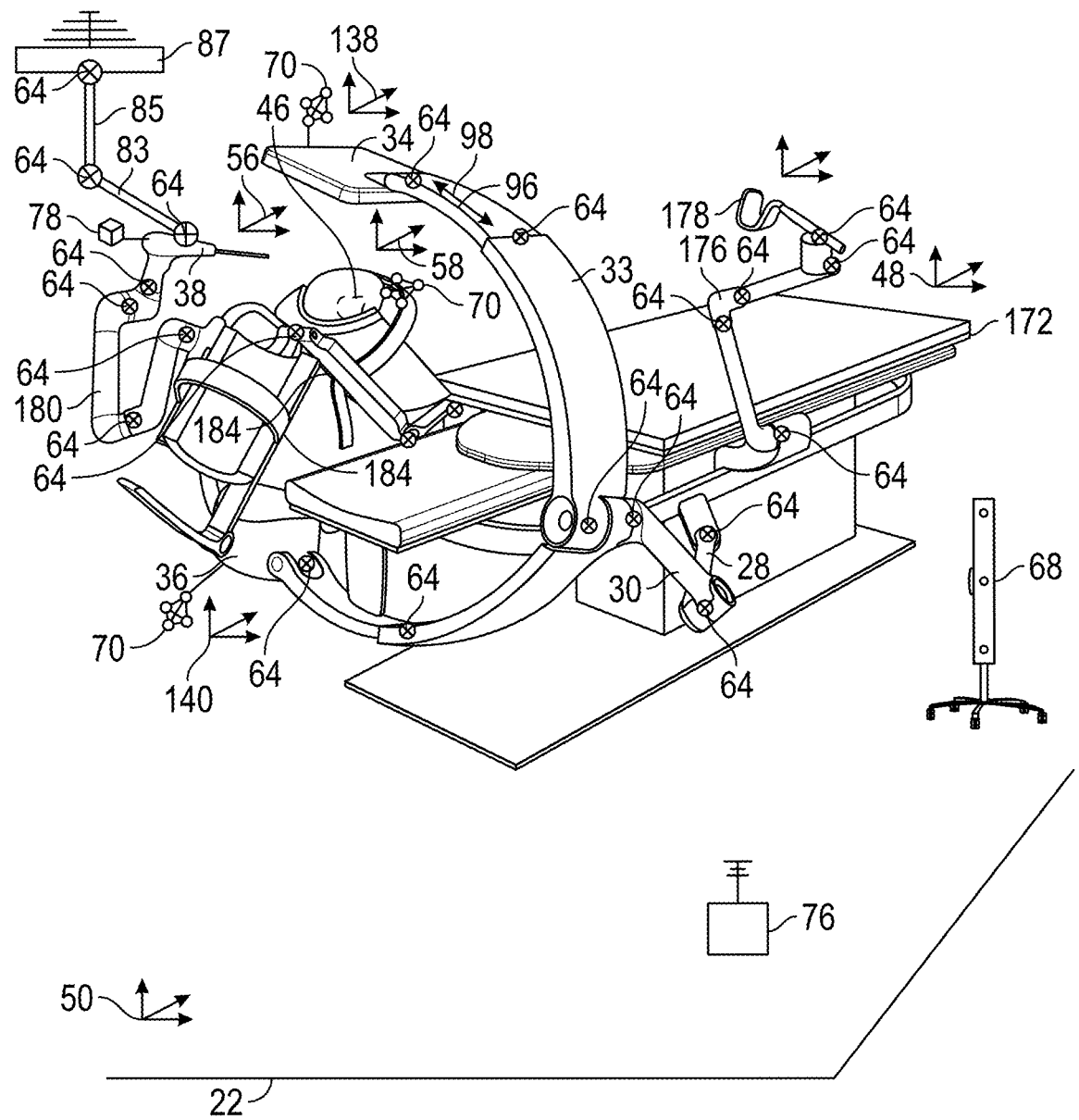
FIG. 12H depicts one embodiment of a robotic surgery system with integrated imaging capabilities.

FIGS. 12G and 12H feature embodiments similar to that of FIG. 12F, with the exception that tracking configurations are also utilized to track the anatomy itself. FIG. 12G shows optical tracking 68/70 with the emitter/detector 68 external to the operational system hardware. FIG. 12H shows the emitter detector 96 integral with the system, i.e., having a portion of the hardware mounted upon one of the arms. An external emitter/detector 68 is also shown and may also be utilized in parallel.

Figure 13:
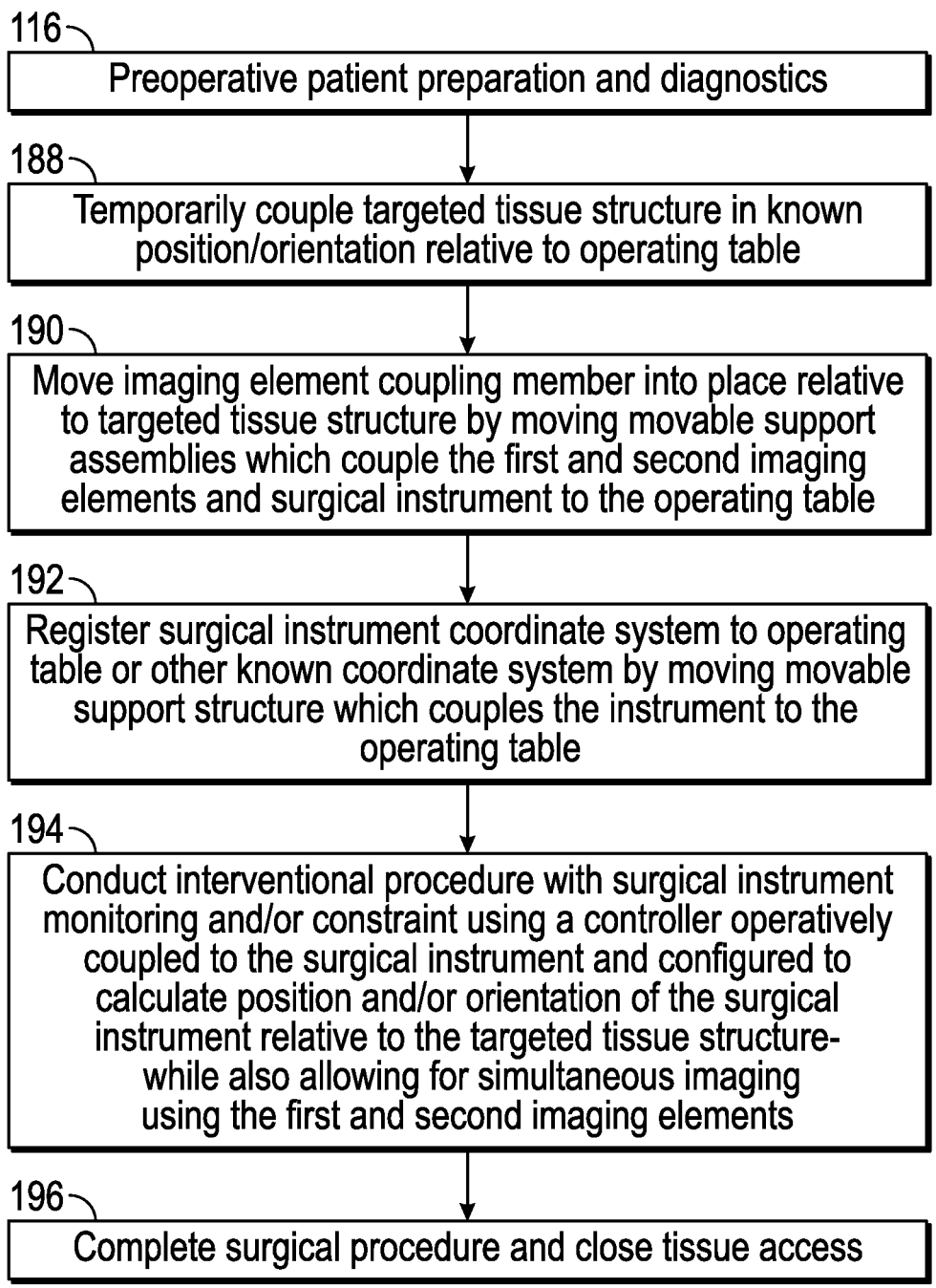
FIG. 13 illustrates one embodiment of a procedure for utilizing an embodiment of a robotic surgery system with integrated imaging capabilities.
Figure 14:
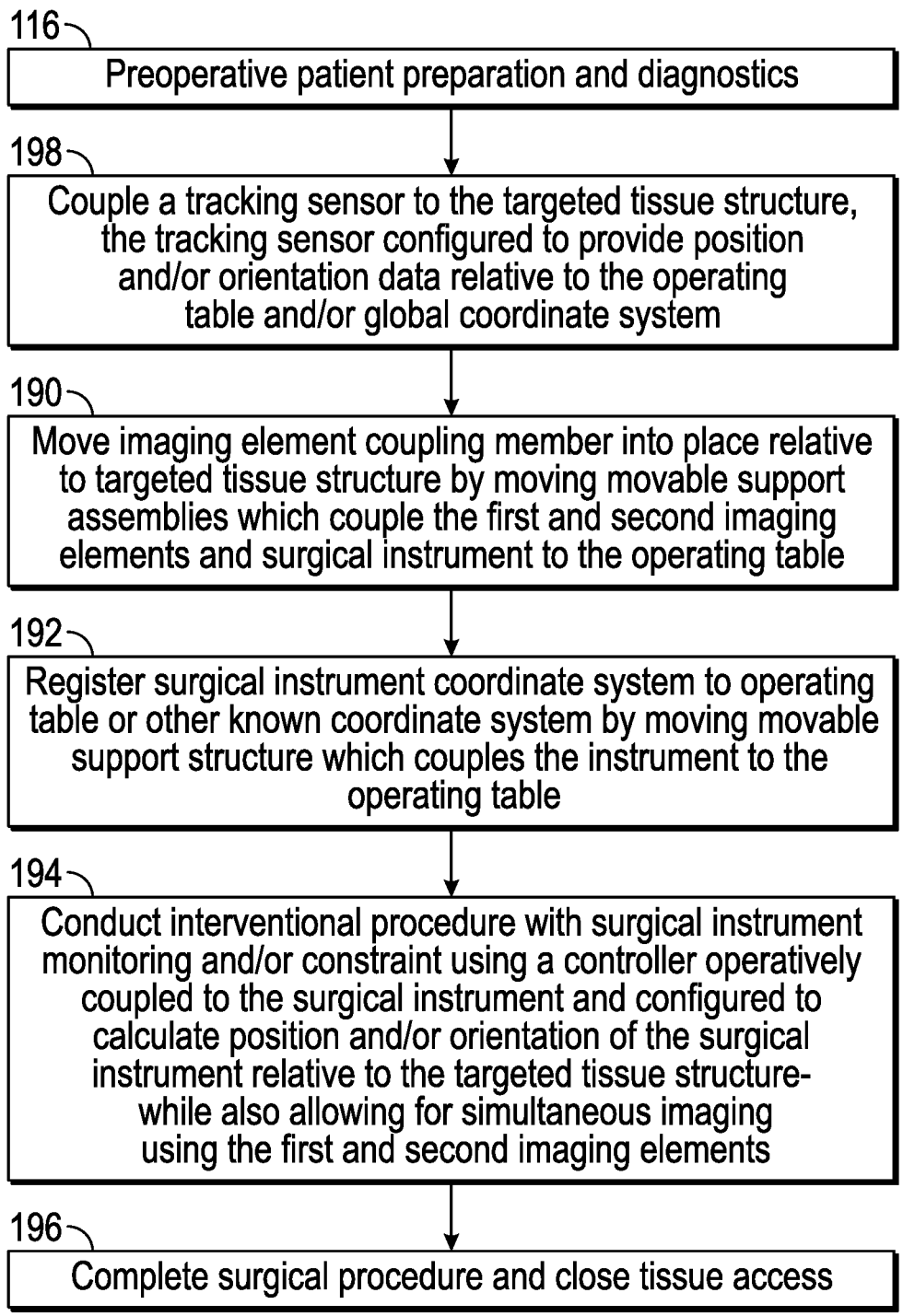
FIG. 14 illustrates one embodiment of a procedure for utilizing an embodiment of a robotic surgery system with integrated imaging capabilities.
Figure 15:
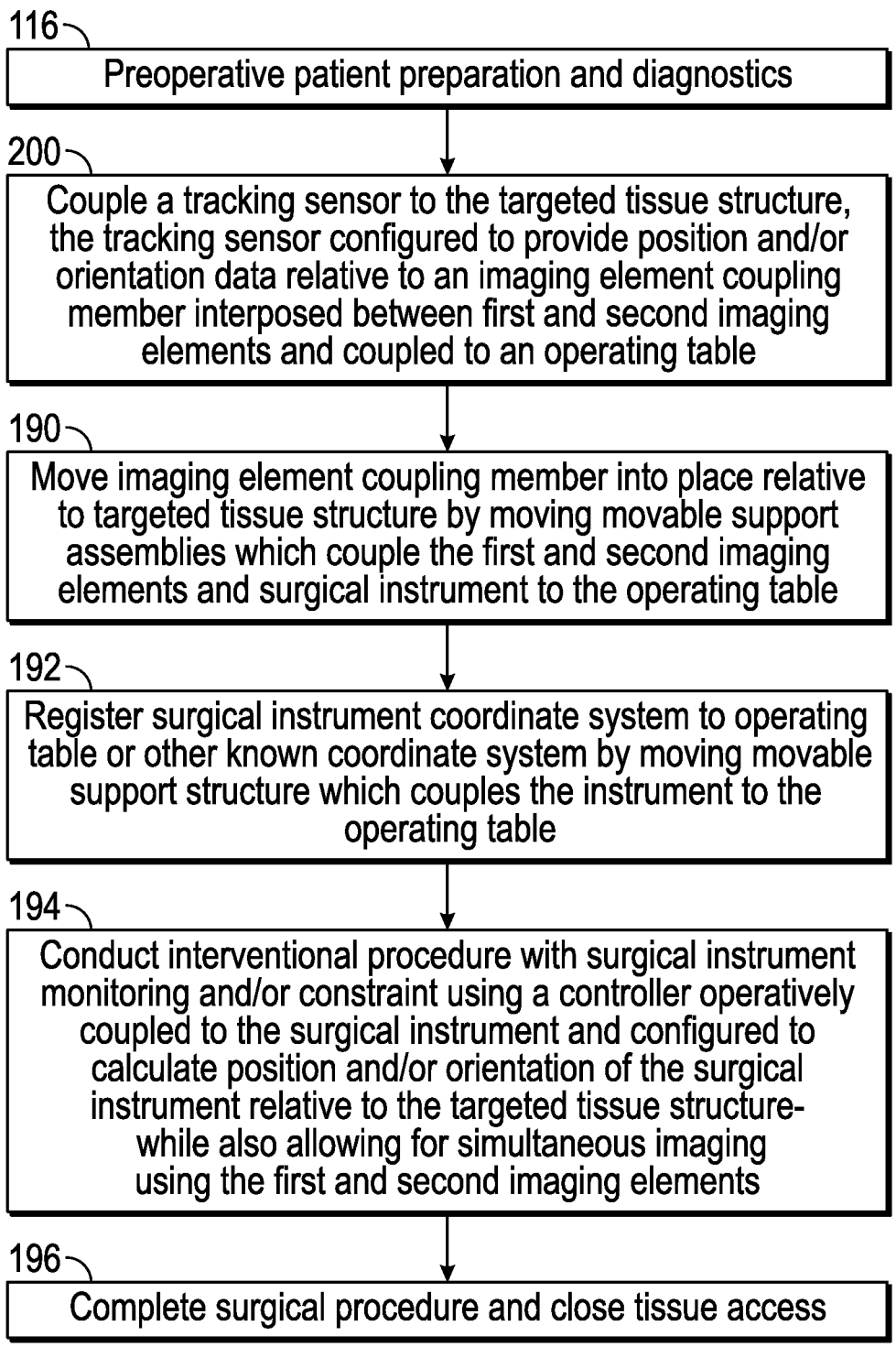
FIG. 15 illustrates one embodiment of a procedure for utilizing an embodiment of a robotic surgery system with integrated imaging capabilities.

Referring to FIGS. 13-15, techniques for utilizing systems such as those depicted in FIGS. 12A-12H are illustrated.

Referring to FIG. 13, after preoperative patient preparation and diagnostics (step 116), in one embodiment the targeted tissue structure, such as a bone or joint of an appendage, is temporarily coupled relative to the operating table in a known position/orientation (step 188). An imaging element coupling member is moved into place by moving the associated support assembly (step 190). The surgical instrument is registered to a known coordinate system (step 192) and the intervention conducted while also allowing for simultaneous imaging using the inherently registered imaging components (step 194), after which the procedure is completed and tissue access closed (step 196).

Referring to FIG. 14, an embodiment similar to that of FIG. 13 is illustrated, with the exception that a tracking sensors (for example, an encoded mechanical tracker, an electromagnetic sensor, an optical sensor, etc.) is coupled directly to the targeted tissue structure (step 198), for example, as described above in reference to FIG. 12G, to characterize the position and/or orientation of the tissue relative to another known coordinate system. In this exemplary technique, after preoperative patient preparation and diagnostics (step 116), a tracking sensor is coupled to the targeted tissue structure (step 198). The tracking sensor is configured to provide position and/or orientation date relative to the operative table and/or global coordinate system (step 198). An imaging element coupling member is moved into place by moving the associated support assembly (step 190). The surgical instrument is registered to a known coordinate system (step 192) and the intervention conducted while also allowing for simultaneous imaging using the inherently registered imaging components (step 194), after which the procedure is completed and tissue access closed (step 196).

Referring to FIG. 15, an embodiment similar to that of FIG. 13 is illustrated, with the exception that a tracking sensors (for example, an encoded mechanical tracker, an electromagnetic sensor, an optical sensor, etc.) is intercoupled between the targeted tissue structure and a portion of the integrated intervention/imaging hardware itself (step 200), for example, as described above in reference to FIG. 12H, to characterize the position and/or orientation of the tissue relative to another known coordinate system. In this exemplary embodiment, after preoperative patient preparation and diagnostics (step 116), a tracking sensor is coupled to the targeted tissue structure (step 200). The tracking sensor is configured to provide position and/or orientation data relative to an imaging element coupling member interposed between first and second imaging elements and coupled to an operating table. An imaging element coupling member is moved into place by moving the associated support assembly (step 190). The surgical instrument is registered to a known coordinate system (step 192) and the intervention conducted while also allowing for simultaneous imaging using the inherently registered imaging components (step 194), after which the procedure is completed and tissue access closed (step 196).

The exemplary systems and methods described herein may be used and implemented as part of a robotic surgery system, such as that described in U.S. Pat. No. 8,010,180, entitled "Haptic Guidance System and Method" issued Aug. 30, 2011, which is hereby incorporated by reference in its entirety.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits' may further include instructions for use and be packaged in sterile trays or containers as commonly employed for such purposes.

The invention includes methods that may be performed using the subject devices. The methods may include the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element-irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A surgery system, comprising:
a mechanical hub;
an anatomy support structure coupled to the mechanical hub and repositionable relative to the mechanical hub;
a first moveable support structure coupled to the mechanical hub;
an imaging system comprising a source element and a detector element, the imaging system coupled to the mechanical hub via the first moveable support structure such that the source element and the detector element are repositionable relative to the anatomy support structure;
a second moveable support structure coupled to the mechanical hub via the anatomy support structure, wherein the second moveable support structure comprises an actuator operable to electromechanically affect movement of the surgical instrument; and
a surgical instrument coupled to the mechanical hub via the second moveable support structure and the anatomy support structure.

2. The surgery system of claim 1, wherein the second moveable support structure is coupled to the mechanical hub via the anatomy support structure.

3. The surgery system of claim 1, wherein the mechanical hub comprises an operating table.

4. The surgery system of claim 1, wherein the second moveable support structure is a robotic arm.

5. The surgery system of claim 1, wherein the first moveable support structure comprises an actuator operable to electromechanically affect movement of the imaging system.

6. The surgery system of claim 1, wherein the anatomy support structure is a leg holder.

7. The surgery system of claim 1, further comprising a tracking system configured to detect motion of at least one of the first moveable support structure and the second moveable support structure.

8. The surgery system of claim 7, further comprising a controller configured to control one or more actuators of at least one of the first moveable support structure or the second moveable support structure based on data from the tracking system.

9. The surgery system of claim 7, wherein the tracking system is further configured to track a position of an anatomical structure of a patient.

10. The surgery system of claim 7, wherein the tracking system uses joint encoders of the first moveable support structure and the second moveable support structure.

11. The surgery system of claim 7, wherein the tracking system is an optical tracking system or an electromagnetic tracking system.

12. The surgery system of claim 1, wherein the imaging system comprises a C-shaped member, the source element and the detector element positioned at opposing ends of the C-shaped member.

13. The surgery system of claim 1, wherein the first moveable support structure and the second moveable support structure are both arms comprising a plurality of joints.

14. A robotic surgery system, comprising:
a leg holder;
an imaging system coupled to the leg holder and comprising a source element and a detector element positionable such that the leg holder is between the source element and the detector element;
a robotic arm mounted on the leg holder such that the robotic arm is coupled to the imaging system via the leg holder; and
a surgical instrument mounted on the robotic arm.

15. The robotic surgery system of claim 14, further comprising an operating table, wherein the leg holder is coupled to the imaging system via the operating table.

16. The robotic surgery system of claim 15, further comprising a moveable support structure, wherein the imaging system is coupled to the operating table via the moveable support structure.

17. The robotic surgery system of claim 14, wherein the surgical instrument is a bone cutting instrument.

18. The robotic surgery system of claim 14, further comprising circuitry configured to determine relative positions of the surgical instrument and anatomy supported by the leg holder and to receive an image of the anatomy from the imaging system.

19. A method, comprising:
providing a surgery system comprising:
an operating table;
an anatomy support structure coupled to the operating table;
an imaging system coupled to the anatomy support structure via the operating table, the imaging system comprising a source element and a detector element positionable such that the anatomy support structure is between the source element and the detector element;
a robotic arm mounted on the anatomy support structure; and
a surgical instrument mounted on the robotic arm;
fixing a position of an anatomical structure using the anatomy support structure;
imaging the anatomical structure with the imaging system;
performing a registration of the surgical instrument relative to an image of the anatomical structure from the imaging system; and
guiding a surgical procedure performed on the anatomical structure with the surgical instrument based on the image from the imaging system and the registration.

20. The method of claim 19, wherein imaging the anatomical structure with the imaging system comprises moving at least one of the source element and the detector element relative to the anatomy support structure.

* * * * *